(12) United States Patent
Brabander et al.

(10) Patent No.: US 11,325,898 B2
(45) Date of Patent: May 10, 2022

(54) SMALL MOLECULE INDUCERS OF AUTOPHAGY

(71) Applicant: Board of Regents, The University of Texas System, Austin, TX (US)

(72) Inventors: Jef De Brabander, Dallas, TX (US); Qiren Liang, Dallas, TX (US); Beth Levine, Dallas, TX (US); Wei-Chung Chiang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 38 days.

(21) Appl. No.: 17/112,980

(22) Filed: Dec. 4, 2020

(65) Prior Publication Data

US 2021/0115024 A1 Apr. 22, 2021

Related U.S. Application Data

(63) Continuation of application No. PCT/US2019/035099, filed on Jun. 2, 2019.

(60) Provisional application No. 62/680,578, filed on Jun. 4, 2018.

(51) Int. Cl.
| | | |
|---|---|---|
| *C07D 405/04* | (2006.01) | |
| *C07D 405/14* | (2006.01) | |
| *C07D 231/06* | (2006.01) | |
| *C07D 403/04* | (2006.01) | |
| *C07D 231/12* | (2006.01) | |
| *C07D 401/04* | (2006.01) | |
| *C07D 413/10* | (2006.01) | |
| *C07D 413/04* | (2006.01) | |
| *C07D 409/04* | (2006.01) | |
| *C07D 405/06* | (2006.01) | |
| *C07D 417/04* | (2006.01) | |
| *C07D 405/12* | (2006.01) | |

(52) U.S. Cl.
CPC .......... *C07D 405/04* (2013.01); *C07D 231/06* (2013.01); *C07D 231/12* (2013.01); *C07D 401/04* (2013.01); *C07D 403/04* (2013.01); *C07D 405/06* (2013.01); *C07D 405/12* (2013.01); *C07D 405/14* (2013.01); *C07D 409/04* (2013.01); *C07D 413/04* (2013.01); *C07D 413/10* (2013.01); *C07D 417/04* (2013.01)

(58) Field of Classification Search
CPC .. C07D 405/04; C07D 231/06; C07D 231/12; C07D 401/04; C07D 403/04; C07D 405/06; C07D 405/12; C07D 405/14; C07D 409/04; C07D 413/04; C07D 413/10; C07D 417/04
USPC ...................................................... 514/227.8
See application file for complete search history.

(56) References Cited

U.S. PATENT DOCUMENTS

2012/0302609 A1* 11/2012 Becker ................... A61P 35/00
548/364.7

* cited by examiner

*Primary Examiner* — Kristin A Vajda
(74) *Attorney, Agent, or Firm* — Richard Aron Osman

(57) ABSTRACT

Small molecule disruptors of Beclin-1/Bcl-2 protein-protein interactions induce autophagy and hence are useful for treating a variety of indications where stimulation of autophagy is therapeutically useful, including cancer, infection immunity, neurodegeneration, longevity.

20 Claims, No Drawings

SMALL MOLECULE INDUCERS OF AUTOPHAGY

This invention was made with government support under Grant Number U19-AI109725 awarded by the National Institutes of Health (NIH). The government has certain rights in the invention.

INTRODUCTION

Macroautophagy (hereafter referred to as autophagy) is a catabolic pathway by which cells sequester unwanted or damaged cellular proteins or organelles through a double membraned structure called the autophagosome. This process is mediated by a set of evolutionarily conserved genes, the autophagy-related (AIG) genes,[1-2] which function in nucleation of the autophagosomal membrane, elongation of the autophagic membrane, sequestration of cytoplasmic constituents, closure of the double membrane, fusion with the lysosome, and degradation of the sequestered contents.

Autophagy plays significant physiological roles in cellular survival and stress adaptation,[3] metabolism,[4] development,[5-6] immunity,[7] protein and organellar homeostasis,[8] and protection against aging.[9] Moreover, several lines of evidence indicate a link between autophagy and mammalian diseases including diabetes, infection, cancer, neurodegenerative diseases, and aging.[3, 9-10] Whole-body or tissue-specific genetic disruption of autophagy in mice leads to multiple pathologies, including tissue abnormalities, aberrant inflammation, impaired immunity, neurodegeneration, and susceptibility to tumorigenesis.[11] In humans, mutations or polymorphisms in autophagy genes are associated with susceptibility to infection, cancer, inflammatory diseases, asthma, cerebral palsy, frontotemporal dementia, amyotrophic lateral sclerosis (ALS), Huntington's disease, and Parkinson's disease.[11-14] Moreover, gain-of-function mutations or enforced expression of autophagy genes in mice have beneficial effects including improved metabolism and tissue function, extended lifespan, neuroprotection, and decreased tumorigenesis.[11, 15-19] Thus, the development of autophagy-inducing agents provide a therapeutic approach to prevent and/or treat certain diseases in clinical medicine.[11, 20-22]

Several drugs that are currently in clinical trials or clinical use are known to induce autophagy[11, 23]; however, the effects of these drugs are pleiotropic and their actions are not limited to the autophagy pathway. Specifically, many drugs enhance autophagy through the modulation of upstream signaling pathways (such as mTOR inhibition, AMPK activation, calcium channel inhibition, and cAMP signaling) but they also regulate diverse downstream biological functions, thereby resulting in non-autophagy-related effects that may limit clinical utility.[21] Therefore, to maximize benefits and minimize toxicity, there is an urgent need for autophagy-inducing agents that selectively target rate-limiting steps in autophagy execution rather than upstream signaling.

One of the key mechanisms that regulates autophagy initiation is the binding of Bcl-2 to Beclin 1, a scaffold protein that is an essential determinant of the activity of the Beclin 1-VPS34 class III phosphatidylinisotol 3 kinase complex.[24-25] During basal conditions, autophagy levels are constrained by the binding of Bcl-2 (or its related family member, Bcl-xL) to Beclin 1. In response to stressful stimuli (such as nutrient starvation,[24, 26] JNK activation,[26] ceramide,[27] or immunological signaling[28]), the disruption of the Beclin 1/Bcl-2 complex leads to autophagy upregulation in vitro. This disruption can be mediated by multi-site phosphorylation of the non-structured loop of Bcl-2,[26] regulatory phosphorylation of the BH3 domain (an amphipathic alpha helix) of Beclin 1 that reduces its affinity for Bcl-2,[29-30] or BH3-only proteins that competitively disrupt Beclin 1/Bcl-2 binding.[31] Genetically engineered mice with mutations in the Bcl-2 phosphorylation sites required for disruption of Beclin 1/Bcl-2 binding are deficient in starvation- and exercise-induced autophagy in vivo, and fail to experience beneficial metabolic effects of long-term exercise training.[32]

Conversely, knock-in mice with a point mutation in Beclin 1 (F123A inhuman protein, F121A in mouse protein) that reduces its binding affinity in vitro for Bcl-2 and Bcl-xL results in increased constitutive autophagy in multiple tissues, including brain, heart, muscle, liver, mammary gland and kidney.[17-19] These mice demonstrate increased longevity and diminished aging-related phenotypes, particularly age-related renal and cardiac pathological changes and age-related spontaneous tumorigenesis. The Beclin 1 knock-in mutation also decreases the accumulation of amyloid oligomers and improves cognitive function and survival in a mouse model of Alzheimers-like disease[18] and decreases the incidence of breast cancer in a mouse model of HER2-driven tumorigenesis.[19]

Thus, there is compelling genetic evidence that Beclin 1/Bcl-2 interaction serves as an important checkpoint for autophagy induction in vivo. Importantly, the long-term disruption of this complex is not only safe in mice, but it also improves healthspan, extends lifespan, and protects against neurodegenerative diseases and cancers. These in vivo findings, taken together with the extensive in vitro data about the role of Beclin 1/Bcl-2 in autophagy regulation,[25, 30] provide a strong rationale for the development of new autophagy-inducing strategies that target Beclin 1/Bcl-2 binding.

An important challenge of this approach is posed by the overlapping modality by which the BH3 domain of the autophagic protein Beclin 1 and that of pro-apoptotic proteins bind to the conserved hydrophobic grooves of Bcl-2/Bcl-xL.[33-34] BH3 mimetics (e.g. ABT-737, ABT-263, ABT-199) have been developed that disrupt Bcl-2 (and/or Bcl-xL) binding of Beclin 1 (and thereby induce autophagy)[31, 35] but they also disrupt binding between anti-apoptotic Bcl-2 family members and pro-apoptotic BH3 domains (and thereby induce apoptosis).[36] These compounds were optimized for their apoptosis-inducing activity and use as potential cancer chemotherapeutic agents. However, from the standpoint of treating infectious diseases and neurodegeneration and preventing aging (as well as other pathophysiological contexts where upregulation of autophagy may be beneficial), it would be desirable to develop agents that selectively disrupt Beclin 1/Bcl-2 binding but not Bcl-2 family member/pro-apoptotic family member binding to selectively induce autophagy (a pro-survival pathway) without inducing apoptosis. This may be technically feasible since the binding affinity of the BH3 domain of Beclin 1 to Bcl-xL is considerably lower than that of pro-apoptotic BH3 family members,[34, 37-38] thus providing a potential therapeutic window for selective disruption of Beclin 1 binding to Bcl-2/Bcl-xL. Furthermore, detailed biochemical and biophysical analyses of BH3 peptide binding to Bcl-2 family members indicate that differences in the precise binding modalities of different BH3 domains exist that might be exploited therapeutically.[33-34, 39] Therefore, we sought to identify novel autophagy-inducing drugs that target the Beclin 1/Bcl-2 interaction without perturbing the binding of Bcl-2 to pro-apoptotic BH3 domain-containing molecules.

We employed a high-throughput screening (HTS) platform using either a cell-based split-luciferase or in vitro AlphaLISA assays to identify novel Beclin 1/Bcl-2 binding inhibitors. Using chemical libraries comprising ~300,000 compounds from the UT Southwestern Medical Center and the Broad Institute of MIT and Harvard, we identified three small molecule compounds that both disrupt Beclin 1/Bcl-2 interaction in the cell-based split-luciferase assay and directly inhibit Beclin 1/Bcl-2 interaction in the in vitro AlphaLISA assay with micromolar IC50 values. These three compounds induce autophagic flux in cells at concentrations that do not decrease cell viability. Our biochemical data indicate that these compounds inhibit the interaction between the BH3 domain of Beclin 1 and Bcl-2 without affecting the interaction between the BH3 domain of the pro-apoptotic protein, Bax, and Bcl-2 or between the BH3-only protein, Bim, and Bcl-2, indicating that these compounds are selective Beclin 1/Bcl-2 inhibitors. Overall, this screening program identified compounds that selectively disrupt Beclin 1/Bcl-2 interaction.

SUMMARY OF THE INVENTION

Autophagy plays a crucial role in cellular homeostasis, development, immunity, tumor suppression, metabolism, prevention of neurodegeneration, and lifespan extension. Thus, pharmacological stimulation of autophagy provides effective approach for preventing or treating certain human diseases and/or aging. Using split-luciferase and AlphaLISA assays and SAR development we developed small molecules that selectively inhibit the Beclin 1/Bcl-2 protein-protein interaction (versus inhibiting other Bcl-2/BH3-domain containing protein-protein interactions that would induce apoptosis). These small molecule disruptors of Beclin-1/Bcl-2 protein-protein interactions induce autophagy and hence are useful for treating a variety of indications where stimulation (induction) of autophagy is therapeutically useful, including cancer, infection (including Zika) immunity, neurodegeneration, longevity.

In aspects the invention provides:
A method of selectively inducing autophagy, comprising treating a person in need thereof with a pharmaceutical composition comprising a compound of structure I;
A method of selectively inhibiting binding of Beclin 1 BH3 domain to anti-apoptotic Bcl-2 BH3 domain, but not binding of pro-apoptotic Bax BH3 domain or pro-apoptotic Bim BH3 protein to Bcl-2 BH3 domain, comprising treating a person in need thereof with a pharmaceutical composition comprising a compound of structure I;
A pharmaceutical composition formulated for administration to a person in need thereof, comprising a compound of structure I; and A compound, excluding library compound SW076956, of structure I:

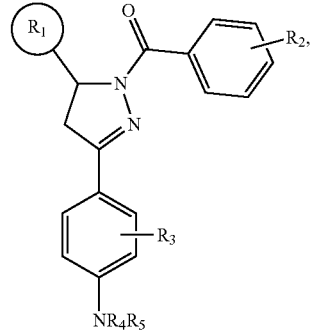

wherein
R1 is optionally substituted C5 or C6 aryl or heteroaryl;
R1 is optionally substituted C5 or C6 aryl or heteroaryl, having 1-3 heteroatoms selected from N, O and S;
R1 is optionally substituted pyrrole, furan, thiophene, imidazole, pyrazole, oxazole, isoxazole, thiazole, isothiazole, triazole, furazan, oxadiazole, thiadiazole, dioxazole, dithiazole, pyridine, pyran, thiopyran, oxazine, thiazine, dioxine, dithiin and triazone; or
R1 is optionally substituted 2- or 3-furanyl or phenyl, 2, 3 or 4-pyridine;
R2 is 0-5 substituents independently selected from optionally substituted heteroatom or optionally substituted, optionally hetero-, optionally cyclic C1-C10 hydrocarbyl;
R2 is 0-5 substituents independently selected from halogen, amide, amine, imine, imide, nitro, nitroso, nitrate, nitrite, cyano, hydroxyl or hydrocarbyloxy, or aldehyde, ketone, carboxyl, ether, ester, alkyl, alkenyl, alkynyl, sulfinyl, sulfonyl;
R2 is 0-5 substituents selected from halogen, $NO_2$, N, C1-C4 alkyl (Me, Et, cPr, iPr, cBu, tBu), C1-C4 alkoxy, C1-C4 carbonyl, C1-C4 carboxyl, C1-C4 cyano, C1-C4 sulfinyl, C1-C4 sulfonyl, each optionally fluorinated; or
R2 is 1 para substituent selected from halogen, $NO_2$, N, C1-C4 alkyl, C1-C4 alkoxy, C1-C4 carbonyl, C1-C4 carboxyl, C1-C4 cyano, C1-C4 sulfinyl, C1-C4 sulfonyl, each optionally fluorinated;
R3 is 0-4 substituents independently selected from optionally substituted heteroatom or optionally substituted, optionally hetero-, optionally cyclic C1-C10 hydrocarbyl;
R3 is 0-4 substituents independently selected from halogen, amide, amine, imine, imide, nitro, nitroso, nitrate, nitrite, cyano, hydroxyl or hydrocarbyloxy, or aldehyde, ketone, carboxyl, ether, ester, alkyl, alkenyl, alkynyl, sulfinyl, sulfonyl;
R3 is 0-4 substituents selected from halogen, $NO_2$, N, C1-C4 alkyl (Me, Et, cPr, iPr, cBu, tBu), C1-C4 alkoxy, C1-C4 carbonyl, C1-C4 carboxyl, C1-C4 cyano, C1-C4 sulfinyl, C1-C4 sulfonyl, each optionally fluorinated; or
R3 is 0 substituents;
R4 is H, optionally substituted heteroatom or optionally substituted, optionally hetero-, optionally cyclic C1-C10 hydrocarbyl, or
R4 is H, hydroxyl or hydrocarbyloxy, or aldehyde, ketone, carboxyl, ether, ester, alkyl, alkenyl, alkynyl, sulfinyl, sulfonyl;

R4 is H or C1-C4 alkyl (Me, Et, cPr, iPr, cBu, tBu), C1-C4 alkoxy, C1-C4 carbonyl, C1-C4 carboxyl, C1-C4 cyano, C1-C4 sulfinyl, C1-C4 sulfonyl, each optionally fluorinated; or R4 is H;

R5 is optionally substituted heteroatom or optionally substituted, optionally hetero-, optionally cyclic C1-C10 hydrocarbyl;

R5 is hydroxyl or hydrocarbyloxy, or aldehyde, ketone, carboxyl, ether, ester, alkyl, alkenyl, alkynyl, sulfinyl, sulfonyl;

R5 is C1-C4 alkyl (Me, Et, cPr, iPr, cBu, tBu), C1-C4 alkoxy, C1-C4 carbonyl, C1-C4 carboxyl, C1-C4 cyano, C1-C4 sulfinyl, C1-C4 sulfonyl, each optionally fluorinated; or R5 is sulfonyl or ester, $SO_2R$ or $CO_2R$, wherein R is C1-C4 alkyl, optionally fluorinated;

wherein R4 and R5 may be joined in a heterocylic ring; or a salt, hydrate, or stereoisomer thereof.

The invention includes all combinations of recited particular embodiments as if each combination had been laboriously recited.

DESCRIPTION OF PARTICULAR EMBODIMENTS OF THE INVENTION

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

Substituents are selected from: halogen, —R', —OR', =O, =NR', =N—OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR'—SO$_2$NR"', —NR"CO$_2$R', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —CN and —NO$_2$, —N$_3$, —CH(Ph)$_2$, perfluoro(C1-C4)alkoxy and perfluoro(C1-C4)alkyl, in a number ranging from zero to three, with those groups having zero, one or two substituents being particularly preferred. R', R" and R"' each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R"', —OC(O)R', —C(O)R', —CO$_2$R', —CONR'R", —OC(O)NR'R", —NR"C(O)R', —NR"CO$_2$R', —NR'—SO$_2$NR"R"', —S(O)R', —SO$_2$R', —SO$_2$NR'R", —NR"SO$_2$R, —CN and —NO$_2$, perfluoro(C1-C4)alkoxy and perfluoro(C1-C4)alkyl, where R' and R" are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The compounds of the invention may also contain unnatural proportions of atomic isotopes at one or more of the atoms that constitute such compounds, such as deuterium, e.g. —CD$_3$, CD$_2$H or CDH$_2$ in place of methyl. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH═C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent R" herein includes from 1 to 4, such as from 1 to 3, further as 1 or 2, substituents selected from the list of R as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, and other reference texts in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent.

Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

It is understood that the examples and embodiments described herein are for illustrative purposes only, not by way of limitation. Those skilled in the art will readily recognize a variety of noncritical parameters that could be changed or modified to yield essentially similar results, and such modifications are included within the spirit and purview of this application and scope of the appended claims. All publications, patents, and patent applications cited herein are hereby incorporated by reference in their entirety for all purposes.

EXAMPLES: GENERAL EXPERIMENTAL

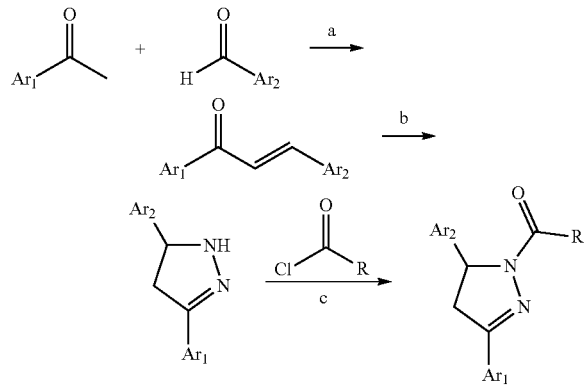

Regent and Conditions: a) KOH MeOH, H$_2$O, room temperature; b) H$_2$NNH$_2$, MeOH, room temperature; c) pyridine, CH$_2$Cl$_2$, room temperature.

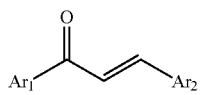

To a solution of methyl aryl ketone compound (1 eq) and KOH (3 eq) in water and MeOH (water:MeOH=1:3) was added aryl carboxaldehyde compound (1.05 eq) at room temperature. The solution was stirred at room temperature for 10 hours, diluted with water, extracted with ethyl acetate. The combined organic extracts was washed with brine, dried over anhydrous Na$_2$SO$_4$, filtered, concentrated in vacuo. The residue was purified by column chromatography (silica gel, gradient elution, EtOAc:Hexane=1:5) to yield the desired product alpha beta unsaturated ketone.

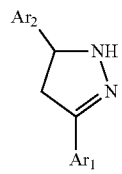

To a solution of alpha beta unsaturated ketone compound (1 eq) in MeOH was added hydrozine (3 eq) at room temperature. The solution was stirred at room temperature for 10 hours, concentrated in vacuo. The residue was washed with water and dried to yield the desired pyrazole product that was used to next step without further purification.

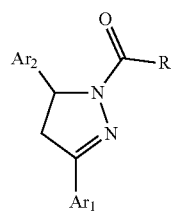

To a solution of pyrazole compound (1 eq) in dichloromethane was added corresponding acid chloride (1.1 eq) and pyridine (1.2 eq) at room temperature. The solution was stirred for 6 hours at room temperature, diluted with ethyl acetate, washed with brine, dried over anhydrous Na$_2$SO$_4$, filtered, concentrated in vacuo. The residue was purified by column chromatography (silica gel, gradient elution, EtOAc:CH$_2$Cl$_2$=1:15) to yield the product.

Activity is retained across the disclosed scope of embodiments of formula, including the scope of R1, R2, R3, R4 and R5, as exemplified in representative compounds show in the tables below.

High Throughput Screens to identify Autophagy Inducers that Function by Disrupting Beclin 1/Bcl-2 Binding Autophagy, a lysosomal degradation pathway, plays a crucial role in cellular homeostasis, development, immunity, tumor suppression, metabolism, prevention of neurodegeneration and lifespan extension. Thus, pharmacological stimulation of autophagy may be an effective approach for preventing or treating certain human diseases and/or aging. We sought to establish a method for developing new chemical compounds that specifically induce autophagy. To do this, we developed two assays to identify compounds that target a key regulatory node of autophagy induction—specifically, the binding of Bcl-2 (a negative regulator of autophagy) to Beclin 1 (an allosteric modulator of the Beclin 1/VPS34 lipid kinase complex that functions in autophagy initiation). These assays use either a split-luciferase assay to measure Beclin 1/Bcl-2 binding in cells or an AlphaLISA assay to directly measure direct Beclin 1/Bcl-2 binding in vitro. We screened two different chemical compound libraries, comprising ~300K compounds, to identify small molecules that disrupt Beclin 1/Bcl-2 binding and induce autophagy. Three novel compounds were identified that directly inhibit Beclin 1/Bcl-2 interaction with an $IC_{50}$ in the micromolar range and increase autophagic flux. These compounds do not demonstrate significant cytotoxicity and they exert selectivity for disruption of Bcl-2 binding to the BH3 domain of Beclin 1 compared to the BH3 domain of the pro-apoptotic Bcl-2 family members, Bax and Bim.

Development of Beclin 1/Bcl-2 Split-Luciferase Assay

To identify novel compounds that disrupt Beclin 1/Bcl-2 interaction, we developed two new HTS assays designed in parallel to (1) identify compounds that have cell penetration activity and function in a cell-based assay to disrupt Beclin 1/Bcl-2 interaction; and (2) identify compounds that disrupt Beclin 1/Bcl-2 binding in vitro and therefore can be verified to function on-target in the cell-based assay.

The first HTS employed a cell-based split-luciferase assay, which is a proximity-based enzyme complementation reporter system. The split-luciferase approach relies on the reconstitution of two fragments of firefly luciferase, NLuc (amino acids 2-416) and CLuc (amino acids 398-550) expressed with proteins of interest as fusion partners. Upon the binding of interacting partners, two non-functional fragments of the luciferase are brought into proximity, forming an active luciferase protein. To measure Beclin 1/Bcl-2 interaction with the split-luciferase assay, we created HeLa cell lines expressing N-terminal NLuc-tagged Beclin 1 (NLuc-Beclin 1) and CLuc-tagged Bcl-2 (CLuc-Bcl-2) as split-luciferase reporters. Both reporters were expressed under the control of a tetracycline-inducible promoter to avoid toxicity or clonal adaptations that might potentially occur as a result of constitutive overexpression of Beclin 1 or Bcl-2. *Renilla* luciferase was constitutively expressed as an internal control. The interaction of Beclin 1/Bcl-2 was measured as relative luminescence units (RLU), which was the calculated ratio of split-luciferase and *Renilla* luciferase signals:

$$\text{Beclin 1/Bcl-2 interaction }(RLU) = \frac{\text{Beclin 1/Bcl-2 Split-Luciferase signal}}{\text{Renilla luciferase signal}}$$

The expression of Beclin 1 and Bcl-2 split-luciferase reporters in HeLa cells yielded measurable luminescence activity that was inhibited in a dose-dependent manner by the positive control compound, ABT-737, a potent BH3 mimetic[40]. To confirm that Beclin 1/Bcl-2 binding is required for the measured split-luciferase activity, we also created cell lines expressing an NLuc-Beclin 1 reporter carrying a deletion of the Bcl-2-binding domain of Beclin 1 (lacking amino acids 81-151; referred to as "Beclin $1^{\Delta Bcl-2BD}$") and CLuc-Bcl-2. The expression of Beclin $1^{\Delta Bcl-2BD}$/Bcl-2 split-luciferase reporters resulted in 10- to 20-fold reduction of luminescence activity and the baseline activity of Beclin $1^{\Delta Bcl-2BD}$/Bcl-2 split-luciferase reporters was not affected by ABT-737. Thus, the full-length Beclin 1/Bcl-2 split-luciferase activity likely represents a specific interaction between the BH3 domain of Beclin 1 and Bcl-2 rather than spontaneous re-association of luciferase fragments. Overall, these data demonstrate that the HeLa cell Beclin 1/Bcl-2 split-luciferase assay is robust and sensitive, providing a wide dynamic range for measuring Beclin 1/Bcl-2 interaction.

We validated the Beclin 1/Bcl-2 split-luciferase assay for HTS with a Z' factor test. The uniformity of the Beclin 1/Bcl-2 split-luciferase assay in a 384-well HTS format was examined. DMSO (240 wells) and ABT-737 (16 wells) were used as neutral or positive controls, respectively. The calculated Z' value was 0.7444, indicating that Beclin/Bcl-2 split-luciferase assay is well-suited for HTS.

Development of Beclin 1/Bcl-2 AlphaLISA Assay

We also developed a high-throughput Beclin 1/Bcl-2 AlphaLISA assay to directly measure the in vitro interaction between Beclin 1 and Bcl-2. AlphaLISA is a bead-based proximity assay that is capable of measuring protein-protein interaction in homogeneous solution.[41] Oxygen singlet molecules are generated by Alpha donor beads upon irradiation at 680 nm and travel to acceptor beads in proximity. Oxygen singlets excite donor beads and result in luminescence emission at 615 nm. The half-life of oxygen singlet molecules is extremely short such that efficient energy transfer occurs only within a radius of 200 nm. Thus, a measurable Alpha luminescence signal requires chemical energy transfer between the donor and acceptor beads, and a pair of interacting molecules immobilized on the beads stabilizes bead association to produce measurable Alpha signals.

We used purified recombinant Beclin 1 and Bcl-2 proteins for AlphaLISA, which were optimized for enhanced solubility and expression. Human Beclin 1 was expressed as a fusion protein with StrepII-SUMO at the N-terminus, and three residues on the aromatic finger of Beclin 1 were mutated (F359D/F360D/W361D) to improve solubility and protein stability.[42] These mutations are in the BARA domain, which is far from the BH3 motif recognized by Bcl-2. A recombinant Bcl-2-binding deficient mutant of Beclin 1 (StrepII-SUMO-Beclin $1^{\Delta Bcl-2BD}$) was used as a negative control. The Bcl-2 construct was composed of amino acids 1-218 and truncated at the transmembrane domain for the addition of a C-terminal 6×His tag (Bcl-2-6×His). For a normalization control, we included a parallel AlphaLISA assay with purified SUMO protein (with an N-terminal StrepII tag and a C-terminal 6×His tag). The purpose of a normalization control is to eliminate inner filter (false-positive) hits that reduce luminescence signal by interfering with the AlphaLISA assay in ways that are unrelated to the Beclin 1/Bcl-2 interaction. With the normalization control, the interaction of Beclin 1 and Bcl-2 was measured as follows:

$$\text{Beclin 1/Bcl-2 interaction} = \frac{\text{Alpha signal}_{Beclin\ 1/Bcl-2}}{\text{Alpha signal}_{SUMO}}$$

The incubation of StrepII-SUMO-Beclin 1 and Bcl-2-6×His with AlphaLISA beads produced a strong Alpha signal. Deletion of the Bcl-2-binding domain of Beclin 1 almost completely abolished the Alpha signal, indicating that the Alpha signal is specific to Beclin 1/Bcl-2 interaction. Furthermore, the strong Alpha signal of Beclin 1/Bcl-2, but not the weak Beclin $1^{\Delta Bcl-2BD}$/Bcl-2 signal, was inhibited in a dose-dependent manner by the BH3 mimetic, ABT-737, which was used as a positive control for the screen.

These data demonstrate that this assay is suitable for measuring pharmacological inhibition of Beclin 1/Bcl-2 binding in vitro. To further evaluate the Beclin 1/Bcl-2 AlphaLISA assay as an HTS platform, we performed a Z' factor test using a 384-well plate format. DMSO (240 wells) and ABT-737 (16 wells) were used as a neutral or positive control, respectively. The resulting Z' value was 0.7237, indicating that the Beclin 1/Bcl-2 AlphaLISA assay is a robust HTS assay.

Primary and Secondary Screens for Disruptors of Beclin 1/Bcl-2 Binding

Using the Beclin 1/Bcl-2 split-luciferase assay, we performed a primary HTS with chemical libraries comprising ~200,000 compounds from UT Southwestern Medical Center (UTSW) and 100,000 compounds derived from diversity-oriented synthesis (DOS) at the Broad Institute of MIT and Harvard.[43] The UTSW chemical library is composed of 75,000 compounds purchased from ChemBridge Corporation, 100,000 compounds purchased from Chemical Diversity Labs, 22,000 compounds from ComGenex, 1200 purchased from TimTek, 1100 purchased from Prestwick, and 450 drugs from the NIH clinical collection. Compounds purchased from TimTek are "natural product-like" synthetic compounds, and the Prestwick compounds are off-patent drugs. The NIH clinical collection is composed of compounds that have been tested in phase I clinical trials. The UTSW chemical library also contains approximately 30,000 natural products isolated from unique marine bacteria by Dr. John MacMillan (UC Santa Cruz). The compounds in the library satisfy a relaxed set of Lipinsky's rules, with 99% having a molecular weight less than 550 g/mol (average 250-300 g/mol). All library compounds were screened at a concentration of 5 µM in a 384-well plate HTS format. During screening, we noticed that a large number of library compounds strongly increased *Renilla* Luciferase activity but did not affect split-luciferase activity. Thus, to eliminate such false-positive hits, we applied a Z-score cut-off of −3.0 on both split-luciferase activity and normalized activity (RLU). Of the identified 1027 hits from the UTSW library and 193 hits from the Broad library, 233 and 55 hits were subsequently confirmed in a repeat HTS assay, respectively.

To identify compounds that directly inhibit Beclin 1/Bcl-2 interaction, a selection of cherry-picked compounds (1027 from the UTSW library and 55 from the Broad library) was subjected to a secondary screen with the Beclin 1/Bcl-2 AlphLISA assay. In the secondary HTS screen, we identified 35 (UTSW library) and one (Broad library) compound which demonstrated >20% (UTSW library) or >40% (Broad library) inhibition with a Z-score ≤−3.0. We resupplied 19 compounds for additional dose-response AlphaLISA (natural product fractions and compounds that were unavailable were excluded). Six of the resupplied compounds were found to inhibit Beclin 1/Bcl-2 interaction in vitro in a dose-dependent manner. After removing pan-assay interference (PAINS)[44] compounds, there were two compounds (SW063058 and SW076956) from the UTSW library and one compound (BRD1991) from the Broad library chosen for further hit validation and biological investigations.

Hit Validation and Assessment of Selectivity

We confirmed that these three candidate compounds showed a dose-dependent inhibition of Beclin 1/Bcl-2 binding at an $IC_{50}$ in the micromolar range using the AlphaLISA. To assess selectivity for disruption of binding of the BH3 domain of Beclin 1 to Bcl-2 as compared to that of a pro-apoptotic Bcl-2 family member, we used an AlphaLISA with purified recombinant Bcl-2 and peptides spanning either the BH3 domain (amino acids 105-130) of Beclin 1 or the BH3 domain (amino acids 49-84) of Bax. Our results indicate that all three candidate molecules decreased the binding of the BH3 domain of Beclin 1 but not the BH3 domain of Bax to Bcl-2. In contrast, ABT-737 inhibited the binding of the BH3 domains of both Beclin 1 and Bax to Bcl-2 with nanomolar efficiency. Although it is still possible that SW063058, SW076956 and BRD1991 might disrupt the binding of Bcl-2 to Bax or other pro-apoptotic BH3 domain-containing molecules at a higher concentration (>20 µM), these data clearly demonstrate a window for selective inhibition of Beclin 1/Bcl-2 interaction.

For the two compounds for which we had sufficient supply for large-scale tissue culture experiments (SW063058 and SW076956), we examined their effects on Beclin 1, Bax, and Bim co-immunoprecipitation with Bcl-2. Using previously described HeLa cells that stably express Myc-tagged Bcl-2[26], we observed that 12 h treatment with SW063058 or SW076956 decreased Beclin 1/Myc-Bcl-2 interaction, but not Bax/Myc-Bcl-2 or Bim/Myc-Bcl-2 interaction. The co-immunoprecipitation experiments in cells showed the same trends as the AlphaLISA in vitro binding experiments; SW076956 is more active than SW063058 in disrupting Beclin 1/Bcl-2 interaction (but not as active as the BH3 mimetic ABT-737) and SW063058 and SW076956, but not ABT-737, selectively disrupt Beclin 1/Bcl-2 versus Bax/Bcl-2 binding. Moreover, ABT-737, but not SW063058 or SW076956, disrupt co-immunoprecipitation between Bcl-2 and the BH3-only protein, Bim.

Functional Assays of Disruptors of Beclin 1/Bcl-2 Binding

The selective activity of SW063058, SW076956, and BRD1991 for disrupting Beclin 1/Bcl-2 binding (versus Bax/Bcl-2 binding) indicated that these compounds may induce autophagy without cell death. We used well-established assays to assess their autophagic activity,[45] including (i) quantitation of GFP-LC3 puncta (which label autophagosomes) in the presence and absence of the lysosomal inhibitor, bafilomycin A1 (Baf A1), and (ii) western blot analysis of the conversion of LC3-I to the lipidated, autophagosomal-associated protein, LC3-II in the presence and absence of Baf A1. HeLa cells stably expressing GFP-LC3 treated with SW063058, SW076956, or BRD1991 had increased numbers of GFP-LC3 puncta as compared to DMSO control 24 h after treatment with 2 µM compound. Shorter durations of lower concentrations of compounds (10 µM) also produced similar results. The numbers of GFP-LC3 puncta increased further in the presence of Baf A1, indicating that these compounds induce complete autophagic flux, rather than a block in autophagolysosomal maturation. In support of these findings, we also found that these compounds induce an increase in LC3-II that further increases in the presence of Baf A1, confirming an increase in autophagic flux. Thus, these compounds induce autophagic flux in HeLa cells.

We assessed whether the induction of autophagy by SW063058 and SW076956 requires Beclin 1 and Bcl-2 using siRNA to knockdown each protein, respectively, in HeLa, cells. Consistent with its role as an essential autophagy protein, Beclin 1 knockdown resulted in decreased autophagosome numbers in baseline conditions (as demonstrated by numbers of GFP-LC3 puncta) and, unlike in cells subjected to control siRNA, there was no further increase in GFP-LC3 puncta upon treatment with SW063058, SW076956 or ABT-737. Consistent with its role as an autophagy inhibitor, Bcl-2 knockdown resulted in increased numbers of GFP-LC3 puncta in baseline conditions and, unlike in cells subjected to control siRNA, there was no further increase in GFP-LC3 puncta upon treatment with SW063058, SW076956 or ABT-737. We confirmed that Beclin 1 knockdown decreased and Bcl-2 knockdown increased, respectively, autophagic flux, by demonstrating increased levels of the autophagic substrate, p62, in cells with Beclin 1 knockdown and decreased levels of the autophagic substrate, p62, in cells with Bcl-2 knockdown. In contrast to cells treated with control siRNA, SW063058, SW076956 or ABT-737 failed to alter p62 levels in cells with either Beclin 1 or Bcl-2 knockdown. Taken together, these data demonstrate that both Beclin 1 and Bcl-2 are required for the autophagy-inducing effects of SW063058, SW076956 and ABT-737.

At the same concentrations that induce autophagic flux (10 and 20 µM) as measured in the GFP-LC3 assay, SW063058 and SW076956 did not exert cytotoxicity in HeLa cells whereas BRD1991 and ABT-737 exerted mild cytotoxicity at 20 µM as measured by CelTiter-Glo assays. Consistent with a previous report indicating that the overexpression of Bcl-2 sensitizes cells to ABT-737-induced apoptosis[46], treatment with ABT-737, but not SW063058, SW076956, or BRD1991, resulted in a more pronounced dose-dependent increase in cell death in HeLa cells that overexpress Bcl-2. We confirmed the CelTiter-Glo results using a more specific assay to detect apoptotic death, the cleavage of the caspase 3 substrate, PARP.[47] A dose-dependent increase in PARP cleavage was observed with ABT-737 treatment, with cleaved PARP detected with 10 or 20 µM compound. At these same concentrations, SW063058, SW076956, and BRD1991 failed to induce PARP cleavage. Altogether, these data indicate that there is a window in which our newly identified disruptors of Beclin 1/Bcl-2 binding induce autophagy without triggering apoptosis or other forms of cell death.

Pharmacokinetic Properties

Given the potential utility of these hits as starting points for further SAR to develop specific autophagy inducers, we analyzed and quantified cell penetration and measured some metabolic stability properties. Using mass spectrometry, we measured the intracellular drug concentration in HeLa cells at different time points after the incubation with 1 µM of either SW063058, SW076956 or BRD1991. All three candidate compounds enter the cell within one hour, but only SW076956 and BRD1991 showed gradual intracellular accumulation over time. In measuring in vitro ADME properties for these hit compounds, microscale thermodynamic solubility showed that the compounds had solubility ranging from 0.72 µM to 30 µM in PBS and 43.3 µM to 202 µM in AlphaLISA buffer. Plasma stability was greater than 90% in murine and human plasma. Murine and human microsomal stability showed that 36% of parental compound SW063058 was unmetabolized after one hour of human microsome extract exposure while all other combinations of compounds exposed to murine or human microsomes were present at concentrations of less 2% of parental compounds after 1 h. Depending on the scaffold chosen to elaborate, these properties will need to be taken into account in moving a series forward.

NMR Chemical Shift Perturbation Analysis

To examine whether SW063058, SW076956 and BRD1991 occupy the hydrophobic pocket of Bcl-2, we carried out a chemical shift perturbation analysis. The incubation of purified Bcl-2/-xL chimera protein (in which the unstructured loop of Bcl-2 was replaced with a short loop from Bcl-xL)[41] with the candidate molecules resulted in chemical shift changes for several residues, indicating that the candidate molecules bind to Bcl-2. Notably, a chemical shift change was observed for F153 located inside the P2 hydrophobic binding pocket of Bcl-2, indicating that these candidate compounds can bind within the BH3 pocket. Other chemical shift changes of residues not in the vicinity of the P2 pocket (G141, V162, and D171) is indicative of allosteric conformational changes of Bcl-2/-xL chimera upon ligand binding. Overall, the chemical shift profiles of SW063058, SW076956 and BRD1991 are similar but showed some distinct features, as compared to known BH3 mimetics, including ABT-737 and ABT-199 and ABT-263. For example, while SW063058, SW076956 and BRD1991 all resulted in a chemical shift in F153 inside the hydrophobic groove (as did the BH3 mimetics), they did not result in chemical shifts in other residues in the groove such as F104 and E136; in addition, SW063058, SW076956 and BRD1991 led to chemical shifts in G155, a residue essential for Bcl-2 binding to Beclin 1,[49] whereas ATB-737 and other BH3 mimetics did not. These data indicate that the structural determinants for the binding of Bcl-2 to our newly identified Beclin 1/Bcl-2 binding disruptors is different from that of known BH3 mimetics.

We have developed two new HTS approaches for identifying compounds that disrupt the Beclin 1/Bcl-2 interaction. These screening tools resulted in the identification of three validated hits, SW063058, SW076956 and BRD1991, that selectively disrupt Beclin 1/Bcl-2 binding as compared to Bax/Bcl-2 and Bim/Bcl-2 binding and induce autophagic flux at concentrations that showed minimal cytotoxicity. Moreover, NMR chemical shift perturbation data indicate that these newly identified compounds can bind to the P2 pocket of Bcl-2 via a modality that is distinct from currently available BH3 mimetics.

A previous screen was recently reported with a smaller number of compounds to identify small molecules that function as Beclin 1 BH3 mimetics and induce both autophagy and apoptosis.[50] In contrast, our goal was to identify compounds that only induce autophagy by exerting selectivity for disrupting the binding of the BH3 domain of Beclin 1 but not the BH3 domain of Bax to Bcl-2. We identified three initial tool compounds that meet these criteria. Although they are biologically active in the micromolar range, the properties identified in this study—especially their selectivity for disrupting the interaction between Bcl-2 and the Beclin 1 BH3 motif, their ability to induce autophagy without cytotoxicity, and their unique NMR chemical shift perturbation profiles (compared to known BH3 mimetics)—rendered them strong hit compounds for design of analogs of increasing potency, increasing selectivity for disrupting Beclin 1/Bcl-2 versus Beclin 1/Bax (or other pro-apoptotic BH3-containing proteins) interaction, and optimizing ADME properties. The cell-based and in vitro based Beclin 1/Bcl-2 binding assays provides a useful both for rapid assessment/optimization of such analogs.

We used these compounds as starting points for the development of effective Beclin 1/Bcl-2 selective inhibitors, and our structure-activity relationship work produced autophagy modulators further described herein.

Cell Lines

HeLa/GFP-LC3[51] and HeLa/Myc-Bcl-2[26] cells were previously described by our laboratory. Beclin 1/Bcl-2 split-luciferase cells were generated by stable transfection of HeLa tet-on cells (Clontech) with the tetracycline-inducible plasmid pTRE2pur vector expressing NLuc-Beclin 1 (or Beclin 1$^{\Delta Bcl-2BD}$ mutant) and the pTRE2-RLuc-hyg3 vector expressing CLuc-Bcl-2. Stable clones were selected in selection medium (DMEM supplemented with DMEM supplemented with 10% Tet-system-approved FBS, 1 mM glutamine, 100 µg/mL G418, 200 µg/mL hygromycin, and 0.5 µg/mL puromycin). The previously described Beclin 1$^{\Delta Bcl-2BD}$ mutant[24, 49] contains a deletion in the Beclin 1 BH3 domain spanning from amino acids 88-150 which interferes with its binding to Bcl-2.

Recombinant Proteins and Peptides

The human beclin 1 gene was cloned into the expression vector ppSUMO-Strep as a fusion with N-terminal StrepII tag and SUMO protein. Three aromatic residues located at the "aromatic finger" of human Beclin 1[42] were mutated to aspartate (F359D/F360D/W361D) to improve protein solubility. *E. coli* BL21 Star (DE3) pLysS containing StrepII-SUMO-Beclin 1, StrepII-SUMO-Beclin 1$^{\Delta Bcl-2BD}$ or StrepII-SUMO-6xHis expression plasmids were grown at 37° C. until logarithmic phase and incubated in 0.1 mM IPTG at 16° C. overnight. Soluble StrepII-SUMO-Beclin 1 or StrepII-SUMO-Beclin 1$^{\Delta Bcl-2BD}$ protein was affinity-purified by StrepTactin sepharose (IBA Biosciences) and further purified by size exclusion chromatography with a HiLoad 16/60 Superdex 200 column (GE Healthcare) equilibrated with Modified Buffer W (100 mM Tris-HCl, pH 8.0, 300 mM NaCl, 5% glycerol, 0.1% CHAPS, and 1 mM DTT).

For the purification of Bcl-2, the expression plasmid pET21c-Bcl-2 (spanning amino acid 1-218), which encodes human Bcl-2 lacking the transmembrane domain with a C-terminal 6xHis tag was used. BL21 Star (DE3) pLysS harboring the expression plasmid was grown at 37° C. until logarithmic phase, and IPTG was added to a final concentration of 0.1 mM and incubated at 16° C. overnight. Soluble Bcl-2-6xHis protein was affinity purified by Ni-NTA agarose (Qiagen) with lysis buffer (50 mM phosphate, pH 8.0, 300 mM NaCl, 0.1% CHAPS and 5% glycerol). Imidazole was used at 10 mM for binding, 20 mM for washing, and 250 mM for elution. The affinity purified Bcl-2-6xHis was further purified by size exclusion chromatography with a HiLoad 16/60 Superdex 200 column equilibrated with Modified Buffer W.

NMR experiments used a chimeric version (Bcl-2/-xL) of Bcl-2 that substitutes the Bcl-xL loop to improve the 2D spectra.[48] DNA was optimized for expression in *E. coli* (GeneArt, Life Technologies) and cloned into a pET28a vector with an N-terminal His$_6$-MBP tag to aid overexpression. A TEV cleavage site was engineered between the MBP tag and Bcl-2/-xL proteins for removal of the MBP-tag. The protein was expressed and labeled as described[52] and protein purification was done as described.[53] Protein purity was estimated to be ≥95% by SDS-PAGE, with image analysis by ImageJ, and quantified using an $\varepsilon_{280}$ of 43,430 M$^{-1}$ cm$^{-1}$. Aliquots were concentrated to 100 μM and frozen at −80° C. until needed.

The Beclin 1 BH3 peptide consists of an N-terminally linked biotin, a YGGGGS linker, and 16 amino acids (a.a. 105-130) derived from human Beclin 1. Bax BH3 peptide consists of an N-terminally linked biotin, a YGGGGS linker, and 36 amino acids (a.a. 49-84) derived from human Bax. Biotin-6xHis control peptide consists of an N-terminally linked biotin, a YGGGGS linker, and a 6xHis tag at C-terminus.

Beclin 1/Bcl-2 Split-Luciferase Screen

Beclin 1/Bcl-2 split-luciferase cells were suspended in induction medium (DMEM supplemented with Tet-approved FBS, 1 mM glutamine, 100 units/mL of Penicillin/Streptomycin, and 1 μg/mL doxycycline) and plated at 1.2×10$^4$ cells/well in 384-well plates (Corning #3570) and incubated at 37° C. overnight.

DMSO (neutral control), ABT-737 (positive control), or the library compounds were added to a final concentration of 5 μM and incubated at 37° C. Compounds were from either the UTSW (200K) or the Broad Institute of MIT and Harvard diversity-oriented synthesis (100K) collection (provided courtesy of Stuart Schreiber). After 5 h of incubation, the medium was removed by centrifugation and the activity of Beclin 1/Bcl-2 split-luciferase reporters was measured with Dual-Glo® Luciferase Assay System (Promega). Twenty microliters of 1×FL buffer (1:1 dilution of Luciferase Reagent with PBS) was first added to the well, incubated at room temperature for 10 min, and firefly luminescence units were measured by an Envision plate reader (Perkin Elmer). Ten microliters of 1×RL buffer (Stop & Glo Reagent) was then added to the sample, the sample was incubated at room temperature for 10 min, and the activity of *Renilla* luciferase was measured again. The Beclin 1/Bcl-2 interaction was measured as relative luminescence units (RLU), calculated as the ratio of split-luciferase and *Renilla* luciferase signals.

The screen was performed in a 384-well format. Each assay plate contained 320 library compounds in column 3 to 22. DMSO was included as a neutral control in column 2 and 23, and ABT-737 was used as a positive control in column 1. For analysis of the primary screen data, numerical readouts obtained from EnVision plate reader were quality controlled and processed using the Assay Analyzer module of the Genedata Screener® Suite. To remove systemic variation bias such as edge effect or plate effect, normalized values (RLU) were corrected with a proprietary pattern detection algorithm in the Assay Analyzer software.[54] Z-scores were calculated from the split-luciferase activity and the corrected normalized activity (RLU) for each compound.[54] The percent activity of a compound at the tested concentration was defined as:

$$\text{Percent Activity } (\%) = \frac{(RLU_{compound} - RLU_{DMSO})}{(RLU_{ABT-737} - RLU_{DMSO})} \times 100\%$$

Compounds having Z-scores less than −3.0 in the split-luciferase activity and the corrected normalized activity (RLU) were advanced for study in the confirmation assays.

The confirmation assay for compounds from the UTSW library was performed in triplicate using compound concentrations of 5 μM. The confirmation assays for compounds from the Broad Institute library were performed at 5 μM with a 2-fold 8-point serial dilution. The values of percent activity in the triplicates for each compound were then condensed to a single value as "condensed activity", the representative single value of the triplicates, using the "Robust Condensing" method in Genedata Screener®. In general, the triplicates were pre-condensed into a pair of values (X and Y) as follows:

Values $(X,Y)$=(Median of Triplicates $m$)±Dispersion

Dispersion=Median $(|X_1-m|,|X_2-m|,|X_3-m|)$

A lower |X−Y| value indicated better data quality. For data points where |X−Y|≤30%, the median of X and Y was used as the condensed activity, which is also the median of the triplicate measurements. Otherwise, a condensing function Max (X,Y) was used to estimate the condensed activity. A robust Z-Score was then calculated for each compound using the following equation:

Robust Z-score =

$$\frac{\text{Condensed Activity}- \text{Median of Neutral Controls } (DMSO)}{\text{Robust Standard Deviation of Neutral Controls } (DMSO)}$$

Compounds having Z-scores less than −3.0 (UTSW library) or dose-response inhibition of split-luciferase activity (Broad Institute library) were considered confirmed.

Beclin 1/Bcl-2 AlphaLISA Screen

All AlphaLISA assays were performed in triplicate in a 384-well format with BB buffer (phosphate-buffered saline supplemented with 0.5% BSA and 1 mM DTT). For the Beclin 1/Bcl-2 AlphaLISA, purified StrepII-SUMO-Beclin 1 was incubated with Bcl-2-6×His proteins at 300 nM and 60 nM, respectively. For internal control AlphaLISA assays, StrepII-SUMO-6×His protein (internal control) was used at 20 nM. Samples containing Beclin 1/Bcl-2 or SUMO proteins were added to AlphaPlates-384 (Perkin Elmer #6005350) by Multidrop and incubated with DMSO (neutral control), ABT-737 (positive control), or library compound at 5 µM (UTSW library) or 10 µM (Broad library) at room temperature for 3 h to allow protein-protein interaction. Following the initial incubation, Strep-Tactin Alpha donor (AS106D) and anti-6×His AlphaLISA acceptor beads (AL128M) were added to a final concentration of 40 µg/mL each and incubated at room temperature in the dark for an additional 1 h. All samples were evaluated in triplicate. Alpha signals were measured by an Envision plate reader (Perkin Elmer). Beclin 1/Bcl-2 Alpha signal was normalized with internal control Alpha signal. The normalized value represents the binding activity of Beclin 1 and Bcl-2. The percent activity of a compound was calculated as the following formula:

$$\text{Percent Activity (\%)} = \frac{(\text{Normalized Alpha signal}_{compound} - \text{Normalized Alpha signal}_{DMSO})}{(\text{Normalized Alpha signal}_{ABT-737} - \text{Normalized Alpha signal}_{DMSO})} \times 100\%$$

The values of percent activity of each compound in triplicates were converted into condensed activity and a robust Z-score was calculated as described in the previous section. Compounds with a Z score less than −3.0 and percent activity >20% (UTSW library) or >40% (Broad Institute library) and were selected for further confirmation with dose-response experiments.

For dose-response AlphaLISA experiments, compounds were serially diluted (2-fold, 7 point) with DMSO and added to BB buffer containing purified recombinant proteins or biotinylated peptides at a final concentration range of 10 µM to 156 nM. Protein or peptide concentrations used in dose-response AlphaLISA experiments were as follows: Beclin1/Bcl-2-300 nM/60 nM; SUMO (internal control for Beclin 1/Bcl-2 AlphaLISA)—20 nM; Beclin 1 BH3/Bcl-2—1000 nM/60 nM; Bax BH3/Bcl-2—100 nM/20 nM; Biotin-6×His (internal control for BH3/Bcl-2 AlphaLISA)—10

Analytical Assays

Solubility was either measured in PBS buffer by the Analytical Group of the Broad Institute or in AlphaLISA reaction buffer by the Preclinical Pharmacology Core Laboratory at UT Southwestern Medical Center. To measure solubility in PBS buffer, each compound was prepared in triplicate at 100 µM in both 100% DMSO and PBS with 1% DMSO. Compounds were allowed to equilibrate at room temperature with a 750 rpm vortex shake for 18 h. After equilibration, samples were analyzed by UPLC-MS (Waters, Milford, Mass.) with compounds detected by SIR detection on a single quadrupole mass spectrometer. The DMSO samples were used to create a two-point calibration curve to which the response in PBS was fit. To measure solubility in AlphaLISA reaction buffer, each compound was prepared in triplicate at 1 mM in PBS containing 0.5% BSA and 1 mM DTT in glass vials. The vials were shaken vigorously (250 rpm) on an orbital shaker for 18 h. The samples were placed in teflon eppendorf tubes and centrifuged at 16,100×g for 10 min. The supernatant was collected and analyzed by a Qtrap 3200 LC-MS/MS system.

Plasma stability was determined at 37° C. at 5 h in both human and mouse plasma. Each compound was prepared in duplicate at 5 µM in plasma diluted 50/50 (v/v) with PBS pH 7.4 (0.95% acetonitrile, 0.05% DMSO). Compounds were incubated at 37° C. for 5 h with a 350-rpm orbital shake with time points taken at 0 h and 5 h. Samples were analyzed by UPLC-MS (Waters, Milford, Mass.) with compounds detected by SIR detection on a single quadrupole mass spectrometer.

Microsomal stability was determined at 37° C. at 60 min in both human and mouse microsomes. Each compound was prepared in duplicate at 1 µM with 0.3 mg/mL microsomes in PBS pH 7.4 (1% DMSO). Compounds were incubated at 37° C. for 60 min with a 350-rpm orbital shake with time points taken at 0 min and 60 min. Samples were analyzed by UPLC-MS (Waters, Milford, Mass.) with compounds detected by SIR detection on a single quadrupole mass spectrometer.

NMR Spectroscopy Experiments

The NMR data were acquired using a Bruker Avance III HD 600 MHz spectrometer equipped with a cryogenic QCI cryoprobe at the Broad Institute. The 2D $^{15}$N-$^{1}$H HSQC and TROSY spectra were collected at 25° C. in the absence or presence of compound. The NMR samples were comprised of 90% H$_2$O/10% D$_2$O in 25 mM HEPES (pH 7.5), 150 mM NaCl and 0.5 mM TCEP. For the chemical shift perturbation experiments with ABT-737, ABT-199, ABT-263, SW063058, SW076956 and BRD1991, aliquots were titrated into the $^{15}$N-labeled Bcl-2/-xL and 2D $^5$N-$^1$H HSQC and TROSY spectra were collected at 25° C. The chemical shift assignments for Bcl-2/-xL were performed as previously described.[48] All of the NMR data were analyzed using SPARKY software.

REFERENCES

1. Yang, Z.; Klionsky, D. J., Mammalian autophagy: core molecular machinery and signaling regulation. *Curr Opin Cell Biol* 2010, 22 (2), 124-31.
2. Mizushima, N.; Yoshimori, T.; Ohsumi, Y., The role of Atg proteins in autophagosome formation. *Annu Rev Cell Dev Biol* 2011, 27, 107-32.
3. Levine, et al., Autophagy in the pathogenesis of disease. *Cell* 2008, 132 (1), 27-42.
4. Kim, K. H.; Lee, M. S., Autophagy—a key player in cellular and body metabolism. *Nat Rev Endocrinol* 2014, 10 (6), 322-37.
5. Levine, B.; Klionsky, D. J., Development by self-digestion: molecular mechanisms and biological functions of autophagy. *Dev Cell* 2004, 6 (4), 463-77.
6. Mizushima, N.; Levine, B., Autophagy in mammalian development and differentiation. *Nat Cell Biol* 2010, 12 (9), 823-30.
7. Wang, R. C.; Levine, B., Calcipotriol induces autophagy in HeLa cells and keratinocytes. *J Invest Dermatol* 2011, 131(4), 990-3.

8. Mizushima, N.; Komatsu, M., Autophagy: renovation of cells and tissues. *Cell* 2011, 147(4), 728-41.
9. Rubinsztein, D. C.; Marino, G.; Kroemer, G., Autophagy and aging. *Cell* 2011, 146 (5), 682-95.
10. Mizushima, N.; Levine, B.; Cuervo, A. M.; Klionsky, D. J., Autophagy fights disease through cellular self-digestion. *Nature* 2008, 451(7182), 1069-75.
11. Levine, B.; Packer, M.; Codogno, P., Development of autophagy inducers in clinical medicine. *J Clin Invest* 2015, 125 (1), 14-24.
12. Jiang, P.; Mizushima, N., Autophagy and human diseases. *Cell Res* 2014, 24 (1), 69-79.
13. Choi, A. M.; Ryter, S. W.; Levine, B., Autophagy in human health and disease. *N Engl J Med* 2013, 368 (19), 1845-6.
14. Xu, J.; Xia, L.; Shang, Q.; Du, J.; Zhu, D.; Wang, Y.; Bi, D.; Song, J.; Ma, C.; Gao, C.; Zhang, X.; Sun, Y.; Zhu, L.; Wang, X.; Zhu, C.; Xing, Q., A variant of the autophagy-related 5 gene is associated with child cerebral palsy. *Front Cell Neurosci* 2017, 11(407), doi: 10.3389/fncel.2017.00407
15. Pyo, J. O.; Yoo, S. M.; Ahn, H. H.; Nah, J.; Hong, S. H.; Kam, T. I.; Jung, S.; Jung, Y. K., Overexpression of Atg5 in mice activates autophagy and extends lifespan. *Nat Commun* 2013, 4, 2300.
16. Decressac, M.; Mattsson, B.; Weikop, P.; Lundblad, M.; Jakobsson, J.; Bjorklund, A., TFEB-mediated autophagy rescues midbrain dopamine neurons from alpha-synuclein toxicity. *Proc Natl Acad Sci USA* 2013, 110 (19), E1817-26.
17. Fernández, A. F.; Sebti, S.; Wei, Y.; Zou, Z.; Shi, M.; McMillan, K. L.; He, C.; Chiang, W.; Ting, T.; Marciano, D. K.; Schiattarella, G. G.; Bhagat, G.; Moe, O. W.; Hu, M.; Levine, B., Disruption of the beclin 1/BCL2 autophagy regulatory complex promotes longevity in mice. *Nature* 2018; in press.
18. Rocchi, A.; Yamamoto, S.; Ting, T.; Fan, Y.; Sadleir, K.; Wang, Y.; Zhang, W.; Huang, S.; Levine, B.; Vassar, R.; He, C., A Becn1 mutation mediates hyperactive autophagic sequestration of amyloid oligomers and improved cognition in Alzheimer's disease. *PLoS Genet* 2017, 13 (8), e1006962.
19. Vega-Rubin-de-Celis, S.; Zou, Z.; Fernandez, A. F.; Xiao, G.; Kim, M.; Levine, B., Increased autophagy blocks HER2-mediated breast tumorigenesis. *Proc Natl Acad Sci USA* 2018, 115 (7), 4176-4180.
20. Rubinsztein, D. C.; Codogno, P.; Levine, B., Autophagy modulation as a potential therapeutic target for diverse diseases. *Nat Rev Drug Discov* 2012, 11(9), 709-30.
21. Galluzzi, L.; Bravo-San Pedro, J. M.; Levine, B.; Green, D. R.; Kroemer, G., Pharmacological modulation of autophagy: therapeutic potential and persisting obstacles. *Nat Rev Drug Discov* 2017, 16 (7), 487-511.
22. Menzies, F. M.; Fleming, A.; Caricasole, A.; Bento, C. F.; Andrews, S. P.; Ashkenazi, A.; Fullgrabe, J.; Jackson, A.; Jimenez Sanchez, M.; Karabiyik, C.; Licitra, F.; Lopez Ramirez, A.; Pavel, M.; Puri, C.; Renna, M.; Ricketts, T.; Schlotawa, L.; Vicinanza, M.; Won, H.; Zhu, Y.; Skidmore, J.; Rubinsztein, D. C., Autophagy and neurodegeneration: Pathogenic mechanisms and therapeutic opportunities. *Neuron* 2017, 93 (5), 1015-1034.
23. Williams, A.; Sarkar, S.; Cuddon, P.; Ttofi, E. K.; Saiki, S.; Siddiqi, F. H.; Jahreiss, L.; Fleming, A.; Pask, D.; Goldsmith, P.; O'Kane, C. J.; Floto, R. A.; Rubinsztein, D. C., Novel targets for Huntington's disease in an mTOR-independent autophagy pathway. *Nat Chem Biol* 2008, 4 (5), 295-305.
24. Pattingre, S.; Tassa, A.; Qu, X.; Garuti, R.; Liang, X. H.; Mizushima, N.; Packer, M.; Schneider, M. D.; Levine, B., Bcl-2 antiapoptotic proteins inhibit Beclin 1-dependent autophagy. *Cell* 2005, 122 (6), 927-39.
25. Decuypere, J. P.; Parys, J. B.; Bultynck, G., Regulation of the autophagic bcl-2/beclin 1 interaction. *Cells* 2012, 1(3), 284-312.
26. Wei, Y.; Pattingre, S.; Sinha, S.; Bassik, M.; Levine, B., JNK1-mediated phosphorylation of Bcl-2 regulates starvation-induced autophagy. *Mol Cell* 2008, 30 (6), 678-88.
27. Pattingre, S.; Bauvy, C.; Carpentier, S.; Levade, T.; Levine, B.; Codogno, P., Role of JNK1-dependent Bcl-2 phosphorylation in ceramide-induced macroautophagy. *The Journal of biological chemistry* 2009, 284 (5), 2719-28.
28. Shi, C. S.; Kehrl, J. H., MyD88 and Trif target Beclin 1 to trigger autophagy in macrophages. *The Journal of biological chemistry* 2008, 283 (48), 33175-82.
29. Zalckvar, E.; Berissi, H.; Mizrachy, L.; Idelchuk, Y.; Koren, I.; Eisenstein, M.; Sabanay, H.; Pinkas-Kramarski, R.; Kimchi, A., DAP-kinase-mediated phosphorylation on the BH3 domain of beclin 1 promotes dissociation of beclin 1 from Bcl-XL and induction of autophagy. *EMBO Rep* 2009, 10 (3), 285-92.
30. Levine, B.; Liu, R.; Dong, X.; Zhong, Q., Beclin orthologs: integrative hubs of cell signaling, membrane trafficking, and physiology. *Trends in cell biology* 2015, 25 (9), 533-44.
31. Maiuri, M. C.; Le Toumelin, G.; Criollo, A.; Rain, J. C.; Gautier, F.; Juin, P.; Tasdemir, E.; Pierron, G.; Troulinaki, K.; Tavernarakis, N.; Hickman, J. A.; Geneste, O.; Kroemer, G., Functional and physical interaction between Bcl-X(L) and a BH3-like domain in Beclin-1. *EMBO J* 2007, 26 (10), 2527-39.
32. He, C.; Bassik, M. C.; Moresi, V.; Sun, K.; Wei, Y.; Zou, Z.; An, Z.; Loh, J.; Fisher, J.; Sun, Q.; Korsmeyer, S.; Packer, M.; May, H. I.; Hill, J. A.; Virgin, H. W.; Gilpin, C.; Xiao, G.; Bassel-Duby, R.; Scherer, P. E.; Levine, B., Exercise-induced BCL2-regulated autophagy is required for muscle glucose homeostasis. *Nature* 2012, 481(7382), 511-5.
33. Feng, W.; Huang, S.; Wu, H.; Zhang, M., Molecular basis of Bcl-xL's target recognition versatility revealed by the structure of Bcl-xL in complex with the BH3 domain of Beclin-1. *J Mol Biol* 2007, 372 (1), 223-35.
34. Oberstein, A.; Jeffrey, P. D.; Shi, Y., Crystal structure of the Bcl-XL-Beclin 1 peptide complex: Beclin 1 is a novel BH3-only protein. *J Biol Chem* 2007, 282 (17), 13123-32.
35. Pedro, J. M.; Wei, Y.; Sica, V.; Maiuri, M. C.; Zou, Z.; Kroemer, G.; Levine, B., BAX and BAK1 are dispensable for ABT-737-induced dissociation of the BCL2-BECN1 complex and autophagy. *Autophagy* 2015, 11(3), 452-9.
36. Opydo-Chanek, M.; Gonzalo, O.; Marzo, I., Multifaceted anticancer activity of BH3 mimetics: Current evidence and future prospects. *Biochem Pharmacol* 2017, 136, 12-23.

37. Sinha, S., Colbert, C. L.; Becker, N.; Wei, Y.; Levine, B., Molecular basis of the regulation of Beclin 1-dependent autophagy by the gamma-herpesvirus 68 Bcl-2 homolog M11. *Autophagy* 2008, 4 (8), 989-97.
38. Ku, B.; Liang, C.; Jung, J. U.; Oh, B. H., Evidence that inhibition of BAX activation by BCL-2 involves its tight and preferential interaction with the BH3 domain of BAX. *Cell Res* 2011, 21(4), 627-41.
39. Su, M.; Mei, Y.; Sanishvili, R.; Levine, B.; Colbert, C. L.; Sinha, S., Targeting gamma-herpesvirus 68 Bcl-2-mediated down-regulation of autophagy. *J Biol Chem* 2014, 289 (12), 8029-40.
40. Oltersdorf, et al. An inhibitor of Bcl-2 family proteins induces regression of solid tumours. *Nature* 2005, 435 (7042), 677-81.
41. Eglen, R. M.; Reisine, T.; Roby, P.; Rouleau, N.; Illy, C.; Bosse, R.; Bielefeld, M., The use of AlphaScreen technology in HTS: current status. *Curr Chem Genomics* 2008, 1, 2-10.
42. Huang, et al, Crystal structure and biochemical analyses reveal Beclin 1 as a novel membrane binding protein. *Cell Res* 2012, 22 (3), 473-89.
43. Schreiber, S. L., Target-oriented and diversity-oriented organic synthesis in drug discovery. *Science* 2000, 287 (5460), 1964-9.
44. Baell, J.; Walters, M. A., Chemistry: Chemical con artists foil drug discovery. *Nature* 2014, 513 (7519), 481-3.
45. Mizushima, N.; Yoshimori, T.; Levine, B., Methods in mammalian autophagy research. *Cell* 2010, 140 (3), 313-26.
46. Merino, et al., Bcl-2, Bcl-x(L), and Bcl-w are not equivalent targets of ABT-737 and navitoclax (ABT-263) in lymphoid and leukemic cells. *Blood* 2012, 119 (24), 5807-16.
47. Nicholson, et al., Identification and inhibition of the ICE/CED-3 protease necessary for mammalian apoptosis. *Nature* 1995, 376 (6535), 37-43.
48. Petros, A. M.; Medek, A.; Nettesheim, D. G.; Kim, D. H.; Yoon, H. S.; Swift, K.; Matayoshi, E. D.; Oltersdorf, T.; Fesik, S. W., Solution structure of the antiapoptotic protein bcl-2. *Proc Natl Acad Sci USA* 2001, 98 (6), 3012-7.
49. Liang, X. H.; Kleeman, L. K.; Jiang, H. H.; Gordon, G.; Goldman, J. E.; Berry, G.; Herman, B.; Levine, B., Protection against fatal Sindbis virus encephalitis by Beclin, a novel Bcl-2-interacting protein. *J Virol* 1998, 72 (11), 8586-96.
50. Yu, J.; Lan, L.; Lewin, S. J.; Rogers, S. A., Roy, A., Wu, X.; Gao, P.; Karanicolas, J.; Aube, J.; Sun, B.; Xu, L., Identification of novel small molecule Beclin 1 mimetics activating autophagy. *Oncotarget* 2017, 8 (31), 51355-51369.
51. Shoji-Kawata, S.; Sumpter, R.; Leveno, M.; Campbell, G. R.; Zou, Z.; Kinch, L.; Wilkins, A. D.; Sun, Q.; Pallauf, K.; MacDuff, D., Huerta, C.; Virgin, H. W.; Helms, J. B., Eerland, R.; Tooze, S. A.; Xavier, R.; Lenschow, D. J.; Yamamoto, A.; King, D.; Lichtarge, O.; Grishin, N. V.; Spector, S. A.; Kaloyanova, D. V.; Levine, B., Identification of a candidate therapeutic autophagy-inducing peptide. *Nature* 2013, 494 (7436), 201-6.
52. Marley, J.; Lu, M.; Bracken, C., A method for efficient isotopic labeling of recombinant proteins. *J Biomol NMR* 2001, 20 (1), 71-5.
53. Ranaghan, M. J.; Durney, M. A.; Mesleh, M. F.; McCarren, P. R., Garvie, C. W.; Daniels, D. S.; Carey, K. L., Skepner, A. P., Levine, B. Perez, J. R., The autophagy-related Beclin-1 protein requires the coiled-coil and BARA domains to form a homodimer with submicromolar affinity. *Biochem* 2017, 56 (51), 6639-6651.
54. Wu, Z.; Liu, D.; Sui, Y., Quantitative assessment of hit detection and confirmation in single and duplicate high-throughput screenings. *J Biomol Screen* 2008, 13 (2), 159-67.

TABLE 1

| | Active compounds | | | | | |
| --- | --- | --- | --- | --- | --- | --- |
| ID | Structure | IC50 (uM) | Log P | ClogP | CLogD | tPSA |
| 1qr-8-175 | 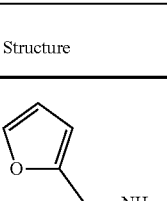 | N/A | −0.27 | 1.582 | 0.62 | 79.79 |

TABLE 1-continued

Active compounds

| ID | Structure | IC50 (uM) | Log P | ClogP | CLogD | tPSA |
|---|---|---|---|---|---|---|
| 1qr-8-177 | 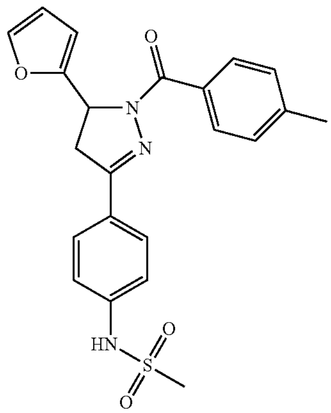 [SMILES: Cc1ccc(C(=O)N2N=C(c3ccc(NS(C)(=O)=O)cc3)CC2c2ccco2)cc1] | 16.17 | 2.07 | 3.076 | 2.7 | 88.07 |
| 1qr-8-178 | 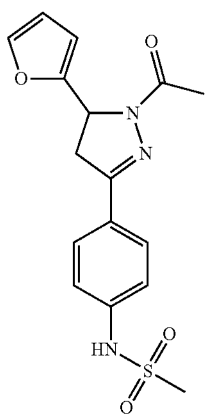 [SMILES: CC(=O)N1N=C(c2ccc(NS(C)(=O)=O)cc2)CC1c1ccco1] | N/A | −0.32 | 1.142 | 0.33 | 88.07 |
| 1qr-8-179 | 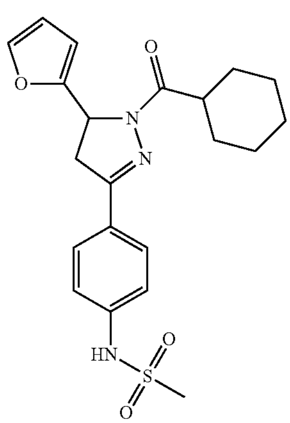 [SMILES: CS(=O)(=O)Nc1ccc(C2=NN(C(=O)C3CCCCC3)C(c3ccco3)C2)cc1] | N/A | 1.66 | 3.173 | 2.45 | 88.07 |

TABLE 1-continued

Active compounds

| ID | Structure | IC50 (uM) | Log P | ClogP | CLogD | tPSA |
|---|---|---|---|---|---|---|
| 1qr-8-180 | 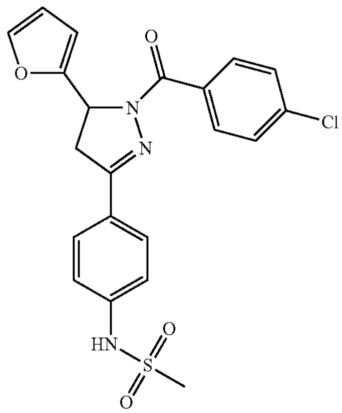 [SMILES: CS(=O)(=O)Nc1ccc(C2=NN(C(=O)c3ccc(Cl)cc3)C(c3ccco3)C2)cc1] | 2.765 | 2.14 | 3.29 | 2.79 | 88.07 |
| 1qr-8-181 | 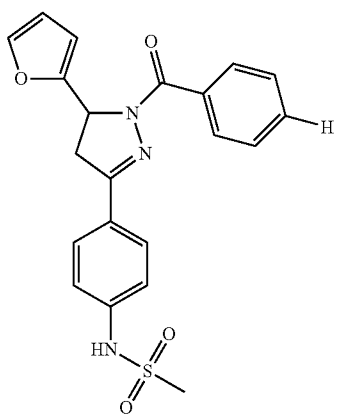 [SMILES: CS(=O)(=O)Nc1ccc(C2=NN(C(=O)c3ccccc3)C(c3ccco3)C2)cc1] | N/A | 1.58 | 2.577 | 2.19 | 88.07 |
| 1qr-8-182 | 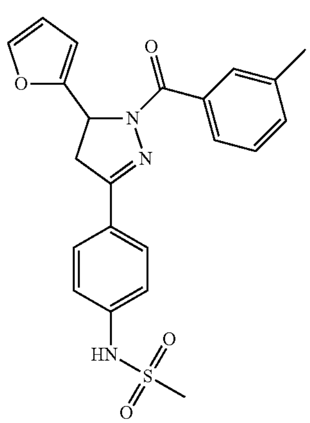 [SMILES: Cc1cccc(C(=O)N2N=C(c3ccc(NS(C)(=O)=O)cc3)CC2c2ccco2)c1] | 18.24 | 2.07 | 3.076 | 2.7 | 88.07 |

TABLE 1-continued

| | Active compounds | | | | | |
|---|---|---|---|---|---|---|
| ID | Structure | IC50 (uM) | Log P | ClogP | CLogD | tPSA |
| 1qr-8-183 | | 12.84 | 1.74 | 2.72 | 2.33 | 88.07 |
| 1qr-8-184 | | N/A | 1.74 | 2.72 | 2.33 | 88.07 |
| 1qr-8-185 | | 9.895 | 1.45 | 2.496 | 2.03 | 97.3 |

TABLE 1-continued

Active compounds

| ID | Structure | IC50 (uM) | Log P | ClogP | CLogD | tPSA |
|---|---|---|---|---|---|---|
| 1qr-8-186 | 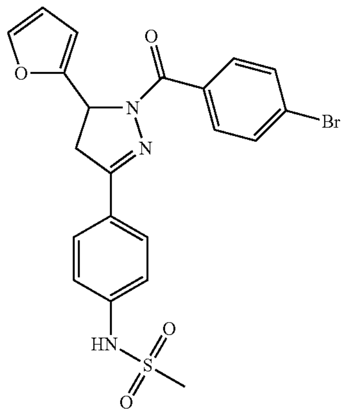 [SMILES: CS(=O)(=O)Nc1ccc(C2=NN(C(=O)c3ccc(Br)cc3)C(c3ccco3)C2)cc1] | 2.421 | 2.41 | 3.44 | 2.96 | 88.07 |
| 1qr-8-187 | 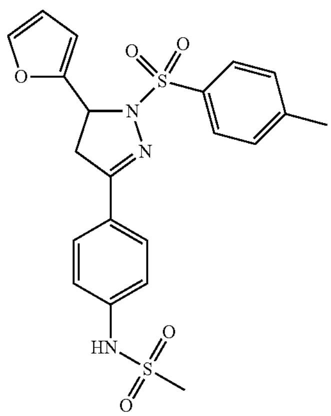 [SMILES: Cc1ccc(S(=O)(=O)N2N=C(c3ccc(NS(C)(=O)=O)cc3)CC2c2ccco2)cc1] | N/A | NA | 2.68 | 2.46 | 105.14 |
| 1qr-8-188 | 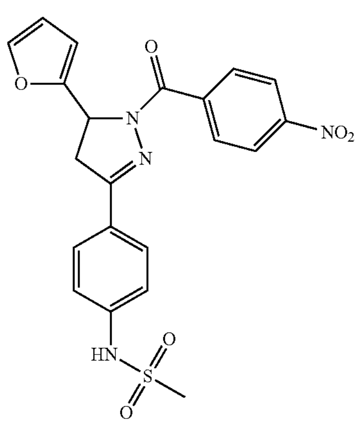 [SMILES: CS(=O)(=O)Nc1ccc(C2=NN(C(=O)c3ccc([N+](=O)[O-])cc3)C(c3ccco3)C2)cc1] | 1.676 | 1.61 | 2.32 | 2.13 | 139.88 |

TABLE 1-continued

Active compounds

| ID | Structure | IC50 (uM) | Log P | ClogP | CLogD | tPSA |
|---|---|---|---|---|---|---|
| 1qr-8-189 | 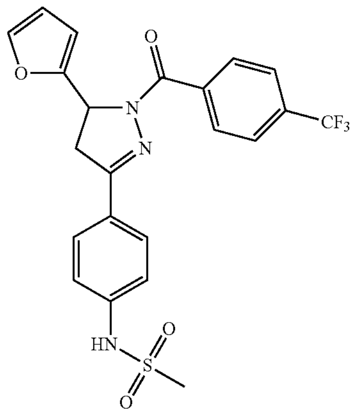 [SMILES: CS(=O)(=O)Nc1ccc(C2=NN(C(=O)c3ccc(C(F)(F)F)cc3)C(c3ccco3)C2)cc1] | 2.794 | 2.5 | 3.46 | 3.07 | 88.07 |
| 1qr-8-190 | 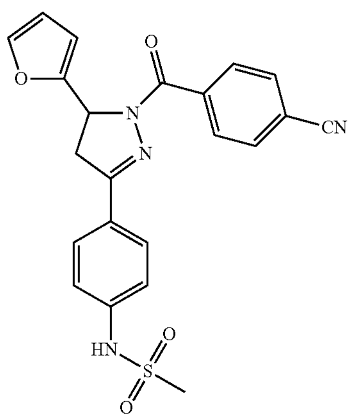 [SMILES: CS(=O)(=O)Nc1ccc(C2=NN(C(=O)c3ccc(C#N)cc3)C(c3ccco3)C2)cc1] | 7.227 | 1.61 | 2.01 | 2.04 | 111.86 |
| 1qr-8-192 | 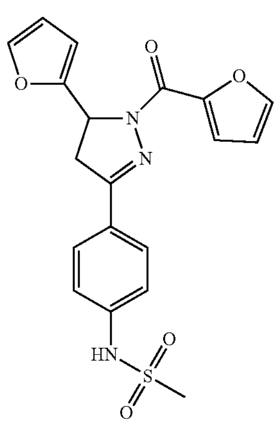 [SMILES: CS(=O)(=O)Nc1ccc(C2=NN(C(=O)c3ccco3)C(c3ccco3)C2)cc1] | N/A | 0.2 | 1.753 | 2.28 | 97.3 |

TABLE 1-continued

Active compounds

| ID | Structure | IC50 (uM) | Log P | ClogP | CLogD | tPSA |
|---|---|---|---|---|---|---|
| 1qr-8-194 | 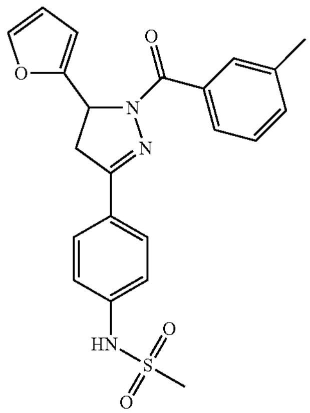 [SMILES: Cc1cccc(C(=O)N2N=C(c3ccc(NS(C)(=O)=O)cc3)CC2c2ccco2)c1] | N/A | 2.19 | 4.909 | 2.8 | 71 |
| 1qr-8-195 | 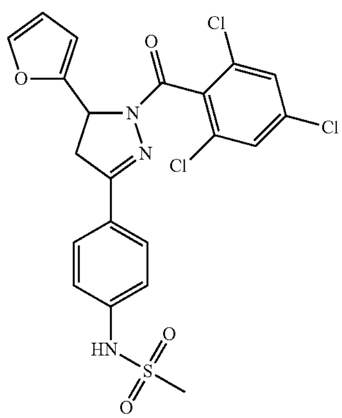 [SMILES: CS(=O)(=O)Nc1ccc(C2=NN(C(=O)c3c(Cl)cc(Cl)cc3Cl)C(c3ccco3)C2)cc1] | N/A | 3.25 | 4.716 | 4 | 88.07 |
| 1qr-8-196 | 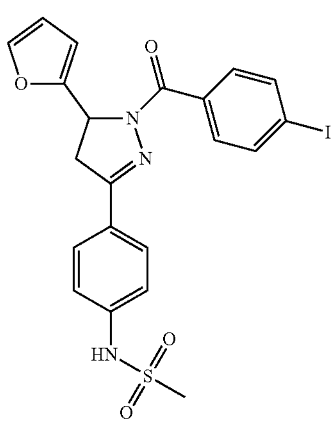 [SMILES: CS(=O)(=O)Nc1ccc(C2=NN(C(=O)c3ccc(I)cc3)C(c3ccco3)C2)cc1] | 2.14 | 2.94 | 3.7 | 3.12 | 88.07 |

TABLE 1-continued
Active compounds
| ID | Structure | IC50 (uM) | Log P | ClogP | CLogD | tPSA |
|---|---|---|---|---|---|---|
| 1qr-8-176 | 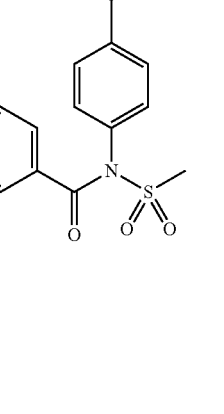 | N/A | 4.4 | 4.81 | 5.06 | 96.35 |
| 1qr-8-203 | 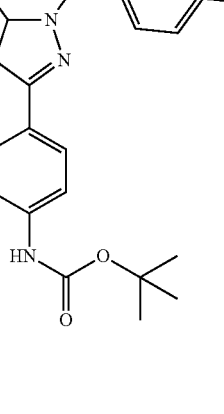 | 2.879 | 4.21 | 4.973 | 5.24 | 80.23 |
| 1qr-8-205 | 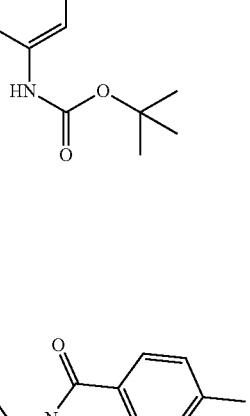 | N/A | 3.04 | 3.04 | 3.48 | 67.92 |

TABLE 1-continued

Active compounds

| ID | Structure | IC50 (uM) | Log P | ClogP | CLogD | tPSA |
|---|---|---|---|---|---|---|
| 1qr-8-211 | 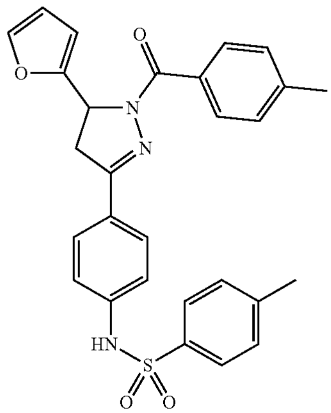 [SMILES: Cc1ccc(C(=O)N2N=C(c3ccc(NS(=O)(=O)c4ccc(C)cc4)cc3)CC2c2ccco2)cc1] | N/A | 4.74 | 5.204 | 5.31 | 88.07 |
| 1qr-8-212 | 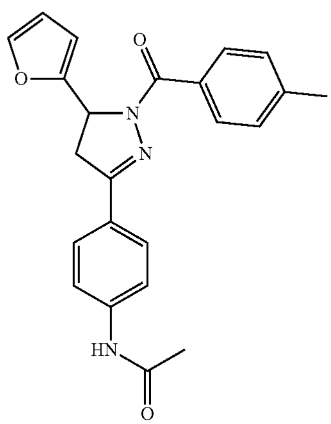 [SMILES: CC(=O)Nc1ccc(C2=NN(C(=O)c3ccc(C)cc3)C(c3ccco3)C2)cc1] | N/A | 2.75 | 3.286 | 3.57 | 71 |
| 1qr-8-214 | 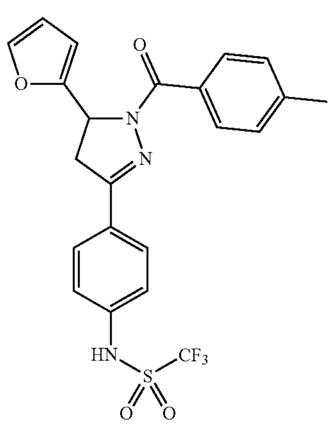 [SMILES: Cc1ccc(C(=O)N2N=C(c3ccc(NS(=O)(=O)C(F)(F)F)cc3)CC2c2ccco2)cc1] | N/A | 4.24 | 5.185 | 3.87 | 88.07 |

TABLE 1-continued

| | Active compounds | | | | | |
|---|---|---|---|---|---|---|
| ID | Structure | IC50 (uM) | Log P | ClogP | CLogD | tPSA |
| 1qr-8-219 | | 29.78 | 3.68 | 4.295 | 4.13 | 53.93 |
| 1qr-8-228 | | N/A | 3.88 | 4.01 | 4.27 | 93.71 |
| 1qr-8-229 | | N/A | 3.72 | 4.186 | 4.17 | 51.13 |
| 1qr-8-230 | | N/A | 4 | 4.41 | 4.47 | 41.9 |

TABLE 1-continued

Active compounds

| ID | Structure | IC50 (uM) | Log P | ClogP | CLogD | tPSA |
|---|---|---|---|---|---|---|
| 1qr-8-235 | 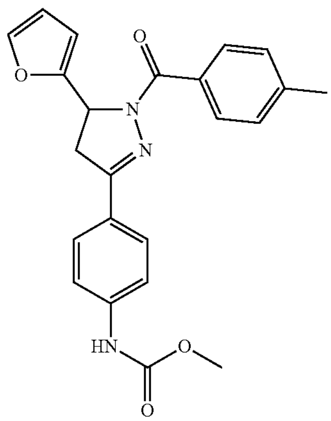 [SMILES: COC(=O)Nc1ccc(C2=NN(C(=O)c3ccc(C)cc3)C(c3ccco3)C2)cc1] | 1.801 | 3.34 | 3.736 | 4.19 | 80.23 |
| 1qr-8-236 | 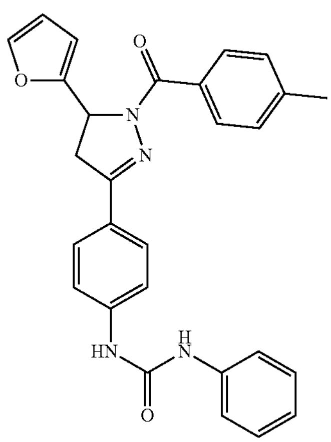 [SMILES: Cc1ccc(C(=O)N2N=C(c3ccc(NC(=O)Nc4ccccc4)cc3)CC2c2ccco2)cc1] | N/A | 4.32 | 5.135 | 5.47 | 83.03 |
| 1qr-8-239 | 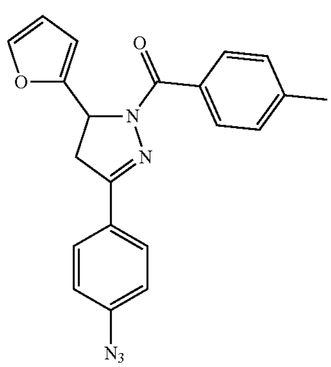 [SMILES: Cc1ccc(C(=O)N2N=C(c3ccc(N=[N+]=[N-])cc3)CC2c2ccco2)cc1] | N/A | 4.63 | 4.71 | 4.63 | 90.66 |

TABLE 1-continued

Active compounds

| ID | Structure | IC50 (uM) | Log P | ClogP | CLogD | tPSA |
|---|---|---|---|---|---|---|
| 1qr-8-240 | 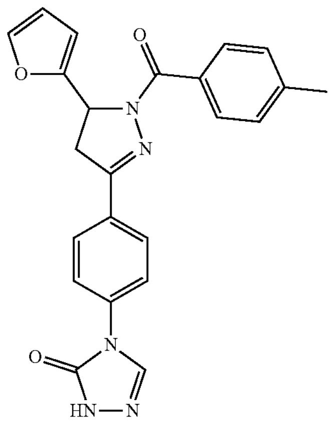 [SMILES: Cc1ccc(C(=O)N2N=C(c3ccc(-n4cn[nH]c4=O)cc3)CC2c2ccco2)cc1] | N/A | 2.9 | 3.652 | 3.63 | 86.6 |
| 1qr-8-241 | 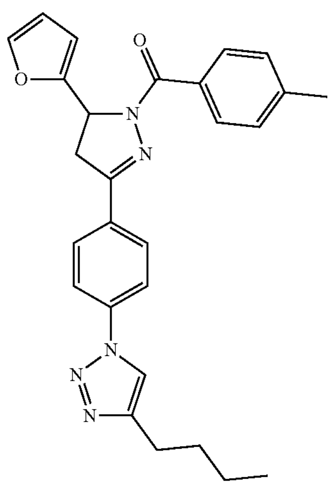 [SMILES: CCCCc1cn(-c2ccc(C3=NN(C(=O)c4ccc(C)cc4)C(c4ccco4)C3)cc2)nn1] | N/A | 5.48 | 5.67 | 5.75 | 69.86 |
| 1qr-8-242 | 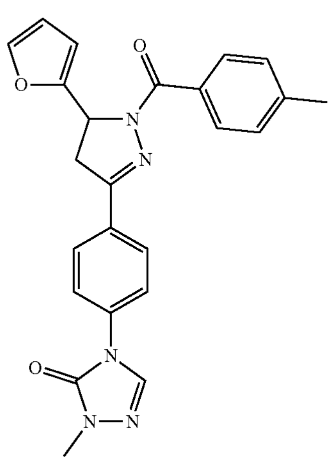 [SMILES: Cc1ccc(C(=O)N2N=C(c3ccc(-n4cnn(C)c4=O)cc3)CC2c2ccco2)cc1] | N/A | 3.14 | 3.483 | 3.85 | 77.81 |

TABLE 1-continued
Active compounds
| ID | Structure | IC50 (uM) | Log P | ClogP | CLogD | tPSA |
|---|---|---|---|---|---|---|
| 1qr-8-231 | 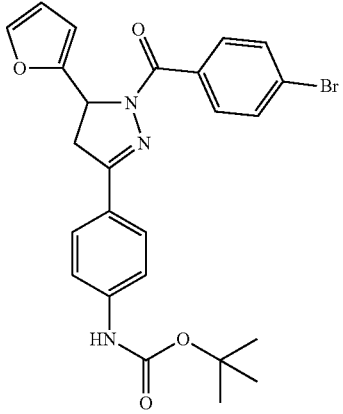 [SMILES: CC(C)(C)OC(=O)Nc1ccc(C2=NN(C(=O)c3ccc(Br)cc3)C(c3ccco3)C2)cc1] | 0.9822 | 4.56 | 5.337 | 5.49 | 80.23 |
| 1qr-8-232 | 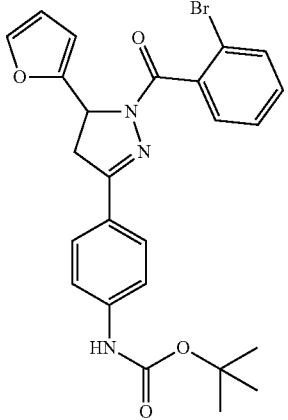 [SMILES: CC(C)(C)OC(=O)Nc1ccc(C2=NN(C(=O)c3ccccc3Br)C(c3ccco3)C2)cc1] | N/A | 4.56 | 5.337 | 5.49 | 80.23 |
| 1qr-8-233 | 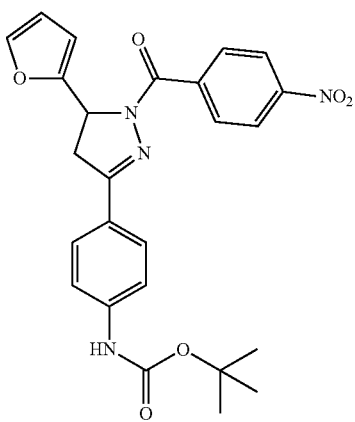 [SMILES: CC(C)(C)OC(=O)Nc1ccc(C2=NN(C(=O)c3ccc([N+](=O)[O-])cc3)C(c3ccco3)C2)cc1] | 1.244 | 3.76 | 4.217 | 4.67 | 132.04 |

TABLE 1-continued

| | Active compounds | | | | | |
|---|---|---|---|---|---|---|
| ID | Structure | IC50 (uM) | Log P | ClogP | CLogD | tPSA |
| 1qr-8-238 | | 0.9048 | 3.45 | 3.9 | 3.64 | 78.84 |
| 1qr-8-267 | | 13.92 | 4.28 | 4.763 | 4.41 | 78.84 |
| 1qr-8-268 | | N/A | 4.28 | 4.763 | 4.41 | 78.84 |

TABLE 1-continued

| | Active compounds | | | | | |
|---|---|---|---|---|---|---|
| ID | Structure | IC50 (uM) | Log P | ClogP | CLogD | tPSA |
| 1qr-8-269 | | 9.83 | 4.28 | 4.763 | 4.41 | 78.84 |
| 1qr-8-275 | | 14.16 | 3.94 | 4.399 | 4.15 | 78.84 |
| 1qr-8-276 | | N/A | 3.49 | 3.643 | 3.58 | 130.65 |

TABLE 1-continued

Active compounds

| ID | Structure | IC50 (uM) | Log P | ClogP | CLogD | tPSA |
|---|---|---|---|---|---|---|
| 1qr-8-278 | 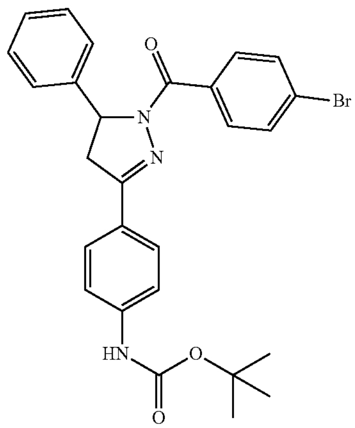 [SMILES: CC(C)(C)OC(=O)Nc1ccc(C2=NN(C(=O)c3ccc(Br)cc3)C(c3ccccc3)C2)cc1] | 0.2741 | 5.94 | 6.161 | 6.43 | 71 |
| 1qr-8-279 | 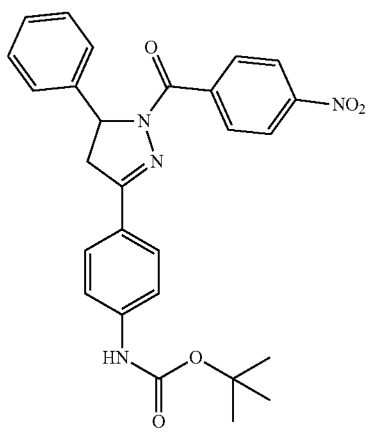 [SMILES: CC(C)(C)OC(=O)Nc1ccc(C2=NN(C(=O)c3ccc([N+](=O)[O-])cc3)C(c3ccccc3)C2)cc1] | 0.3493 | 5.14 | 5.041 | 5.61 | 122.81 |
| Lqr-8-296 | 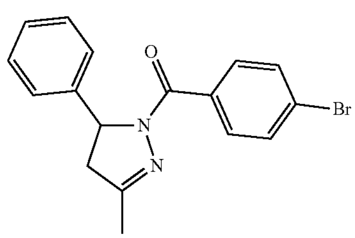 [SMILES: CC1=NN(C(=O)c2ccc(Br)cc2)C(c2ccccc2)C1] | >10 | 4.43 | 4.02 | 4.1 | 32.67 |
| 1qr-8-302 | 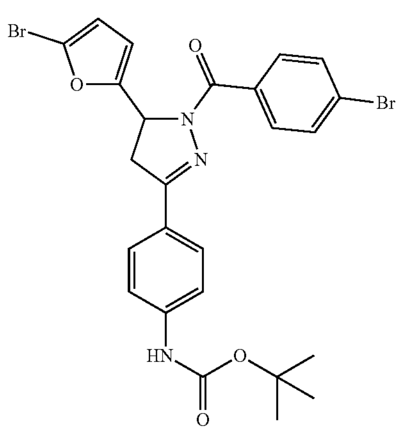 [SMILES: CC(C)(C)OC(=O)Nc1ccc(C2=NN(C(=O)c3ccc(Br)cc3)C(c3ccc(Br)o3)C2)cc1] | 2.68 | 5.26 | 6.2 | 5.96 | 80.23 |

TABLE 1-continued

| Active compounds | | | | | | |
|---|---|---|---|---|---|---|
| ID | Structure | IC50 (uM) | Log P | ClogP | CLogD | tPSA |
| 1qr-8-309 | | >10 | 4.19 | 4.63 | 4.58 | 41.9 |
| 1qr-8-310 | | >10 | 4.12 | 4.06 | 4.52 | 44.7 |
| 1qr-9-004 | | >10 | 3.82 | 3.66 | 4.51 | 105.14 |
| 1qr-9-008 | | 10 | 5.07 | 4.92 | 5.38 | 71 |

TABLE 1-continued

Active compounds

| ID | Structure | IC50 (uM) | Log P | ClogP | CLogD | tPSA |
|---|---|---|---|---|---|---|
| 1qr-9-012 | 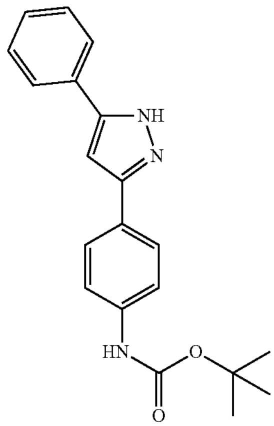 [SMILES: CC(C)(C)OC(=O)Nc1ccc(-c2cc(-c3ccccc3)[nH]n2)cc1] | >10 | 4.33 | 5.27 | 4.79 | 62.72 |
| 1qr-9-013 | 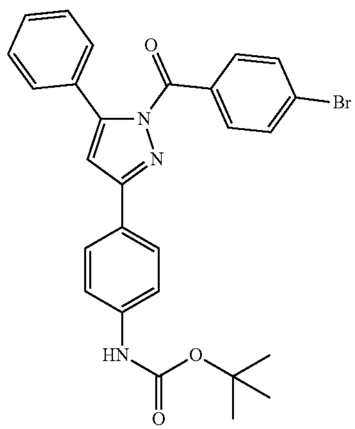 [SMILES: CC(C)(C)OC(=O)Nc1ccc(-c2cc(-c3ccccc3)n(C(=O)c3ccc(Br)cc3)n2)cc1] | >10 | 6.73 | 8.76 | 6.73 | 71 |
| 1qr-9-018 | 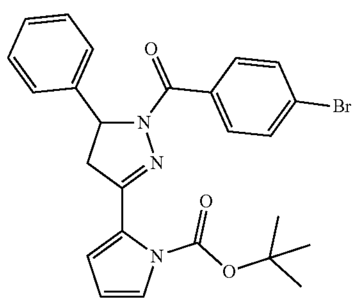 [SMILES: CC(C)(C)OC(=O)n1cccc1C1=NN(C(=O)c2ccc(Br)cc2)C(c2ccccc2)C1] | >10 | 5.52 | 5.75 | 5.52 | 62.21 |
| 1qr-9-026 | 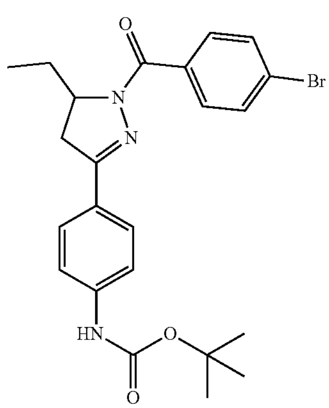 [SMILES: CCC1CC(c2ccc(NC(=O)OC(C)(C)C)cc2)=NN1C(=O)c1ccc(Br)cc1] | 13 | 5.03 | 5.45 | 5.59 | 71 |

TABLE 1-continued

Active compounds

| ID | Structure | IC50 (uM) | Log P | ClogP | CLogD | tPSA |
|---|---|---|---|---|---|---|
| 1qr-9-033 | 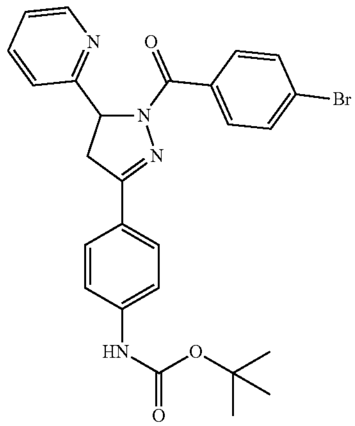 [SMILES: CC(C)(C)OC(=O)Nc1ccc(C2=NN(C(=O)c3ccc(Br)cc3)C(c3ccccn3)C2)cc1] | 0.455 | 5.03 | 4.66 | 5.45 | 83.36 |
| 1qr-9-044 | 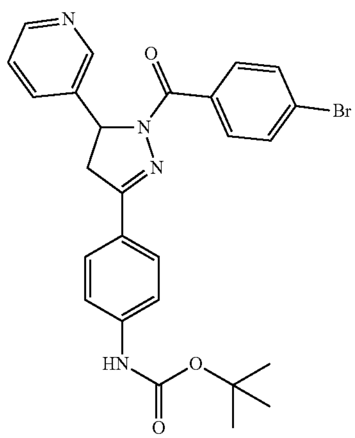 [SMILES: CC(C)(C)OC(=O)Nc1ccc(C2=NN(C(=O)c3ccc(Br)cc3)C(c3cccnc3)C2)cc1] | 1.8 | 4.6 | 4.66 | 5.22 | 83.36 |
| 1qr-9-046 | 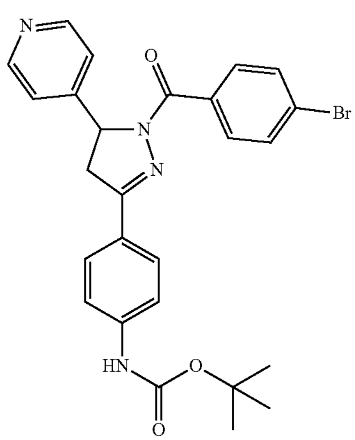 [SMILES: CC(C)(C)OC(=O)Nc1ccc(C2=NN(C(=O)c3ccc(Br)cc3)C(c3ccncc3)C2)cc1] | 3 | 4.6 | 4.66 | 5.21 | 83.36 |

TABLE 1-continued
Active compounds
| ID | Structure | IC50 (uM) | Log P | ClogP | CLogD | tPSA |
|---|---|---|---|---|---|---|
| 1qr-9-048 | 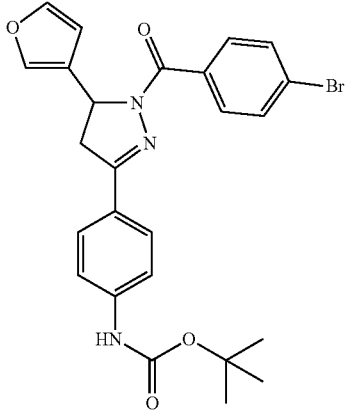 [SMILES: CC(C)(C)OC(=O)Nc1ccc(C2=NN(C(=O)c3ccc(Br)cc3)C(c3ccoc3)C2)cc1] | 4.1 | 4.5 | 5.33 | 5.57 | 80.23 |
| 1qr-9-055 | 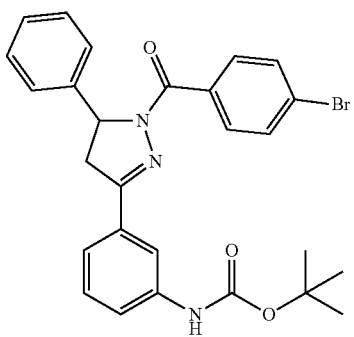 [SMILES: CC(C)(C)OC(=O)Nc1cccc(C2=NN(C(=O)c3ccc(Br)cc3)C(c3ccccc3)C2)c1] | 12 | 5.94 | 6.16 | 6.43 | 71 |
| 1qr-9-056 | 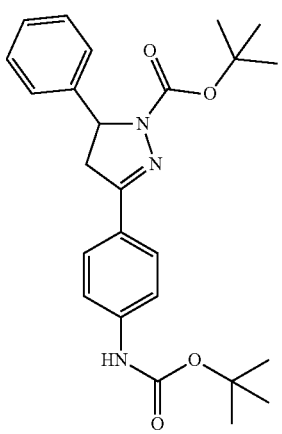 [SMILES: CC(C)(C)OC(=O)Nc1ccc(C2=NN(C(=O)OC(C)(C)C)C(c3ccccc3)C2)cc1] | 10 | 4.67 | 5.53 | 5.48 | 80.23 |

TABLE 1-continued

| | Active compounds | | | | | |
|---|---|---|---|---|---|---|
| ID | Structure | IC50 (uM) | Log P | ClogP | CLogD | tPSA |
| Lqr-9-065 | | 6.77 | 4.89 | 5.26 | 5.29 | 89.46 |
| 1qr-9-073 | | >10 | 5.57 | 5.29 | 6.36 | 88.07 |
| 1qr-9-076 | | 0.3494 | 5.04 | 5.25 | 5.42 | 73.8 |

TABLE 1-continued
Active compounds
| ID | Structure | IC50 (uM) | Log P | ClogP | CLogD | tPSA |
|---|---|---|---|---|---|---|
| 1qr-9-085 | 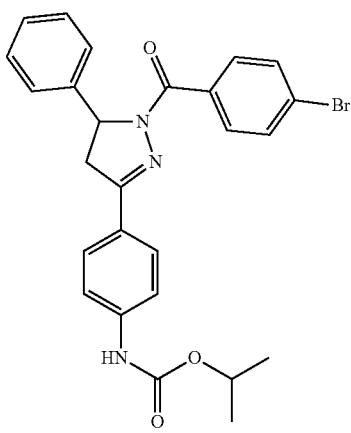 [SMILES: CC(C)OC(=O)Nc1ccc(C2=NN(C(=O)c3ccc(Br)cc3)C(c3ccccc3)C2)cc1] | 0.063 | 5.72 | 5.76 | 6.15 | 71 |
| 1qr-9-088 | 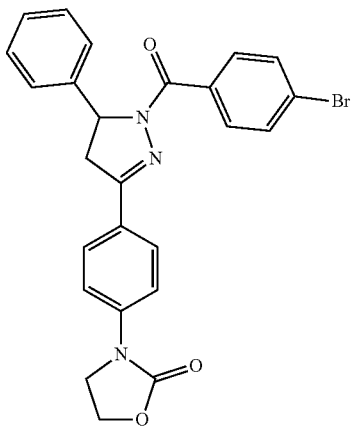 [SMILES: O=C1OCCN1c1ccc(C2=NN(C(=O)c3ccc(Br)cc3)C(c3ccccc3)C2)cc1] | 5.138 | 5.06 | 4.46 | 5.07 | 62.21 |
| 1qr-9-118 | 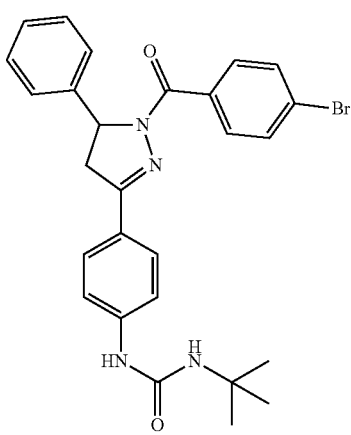 [SMILES: CC(C)(C)NC(=O)Nc1ccc(C2=NN(C(=O)c3ccc(Br)cc3)C(c3ccccc3)C2)cc1] | 9.1 | 5.26 | 5.65 | 5.71 | 73.8 |

TABLE 1-continued

Active compounds

| ID | Structure | IC50 (uM) | Log P | ClogP | CLogD | tPSA |
|---|---|---|---|---|---|---|
| 1qr-9-121 | 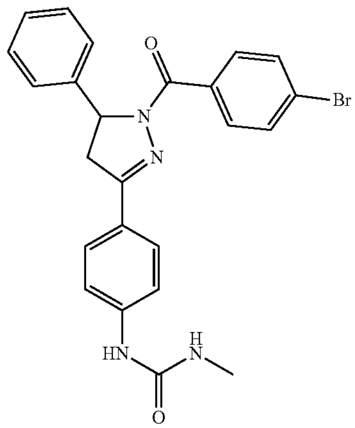 [SMILES: CNC(=O)Nc1ccc(C2=NN(C(=O)c3ccc(Br)cc3)C(c3ccccc3)C2)cc1] | 5.52 | 4.39 | 4.41 | 4.65 | 73.8 |
| 1qr-9-136 | 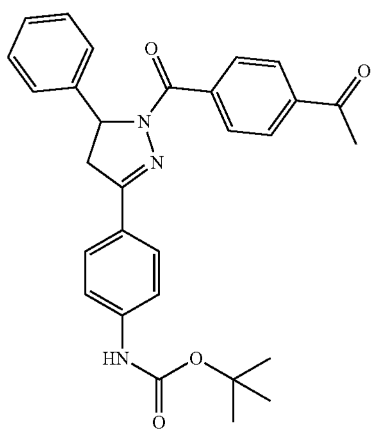 [SMILES: CC(=O)c1ccc(C(=O)N2N=C(c3ccc(NC(=O)OC(C)(C)C)cc3)CC2c2ccccc2)cc1] | 7.5 | 4.42 | 4.74 | 5.22 | 88.07 |
| 1qr-9-068 | 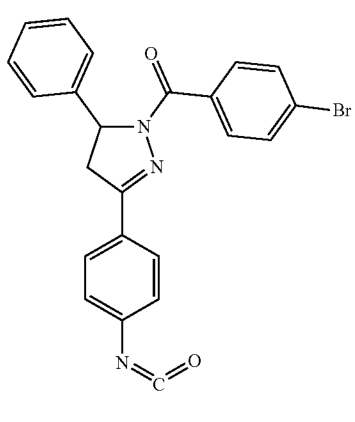 [SMILES: O=C=Nc1ccc(C2=NN(C(=O)c3ccc(Br)cc3)C(c3ccccc3)C2)cc1] | >10 | | 5.77 | 5.43 | 62.1 |

TABLE 1-continued

Active compounds

| ID | Structure | IC50 (uM) | Log P | ClogP | CLogD | tPSA |
|---|---|---|---|---|---|---|
| 1qr-9-155 | 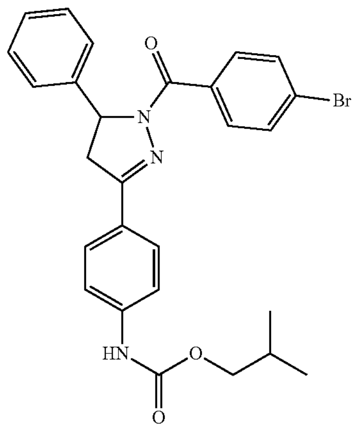 [SMILES: CC(C)COC(=O)Nc1ccc(C2=NN(C(=O)c3ccc(Br)cc3)C(c3ccccc3)C2)cc1] | 0.184 | 6.29 | 6.38 | 6.62 | 71 |
| 1qr-9-156 | 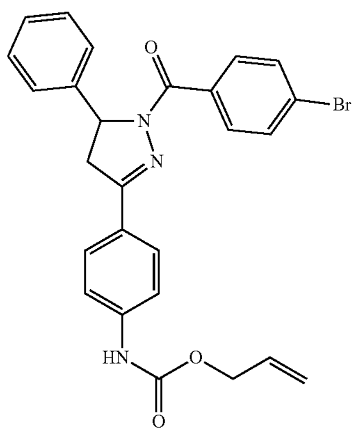 [SMILES: C=CCOC(=O)Nc1ccc(C2=NN(C(=O)c3ccc(Br)cc3)C(c3ccccc3)C2)cc1] | <0.156 | 5.76 | 5.7 | 6.11 | 71 |
| 1qr-9-157 | 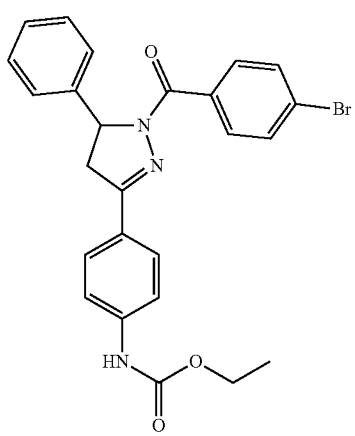 [SMILES: CCOC(=O)Nc1ccc(C2=NN(C(=O)c3ccc(Br)cc3)C(c3ccccc3)C2)cc1] | <0.156 | 5.4 | 5.45 | 5.74 | 71 |

TABLE 1-continued

Active compounds

| ID | Structure | IC50 (uM) | Log P | ClogP | CLogD | tPSA |
|---|---|---|---|---|---|---|
| 1qr-9-158 | 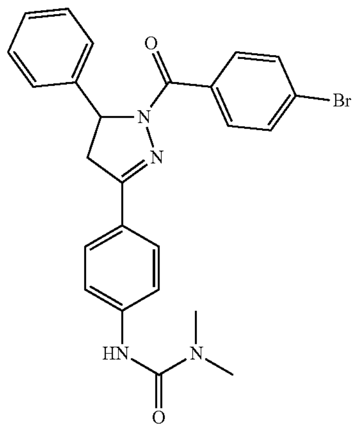 [SMILES: CN(C)C(=O)Nc1ccc(C2=NN(C(=O)c3ccc(Br)cc3)C(c3ccccc3)C2)cc1] | 2.39 | 4.62 | 4.29 | 4.87 | 65.01 |
| 1qr-9-161 | 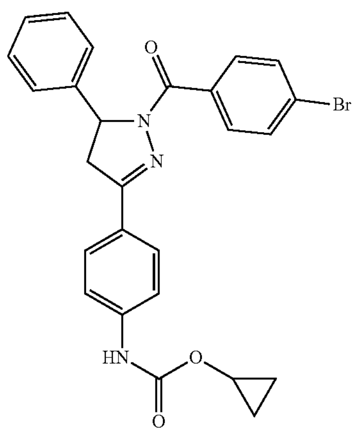 [SMILES: O=C(Nc1ccc(C2=NN(C(=O)c3ccc(Br)cc3)C(c3ccccc3)C2)cc1)OC1CC1] | <0.156 | 5.36 | 5.51 | 5.85 | 71 |
| 1qr-9-163 | 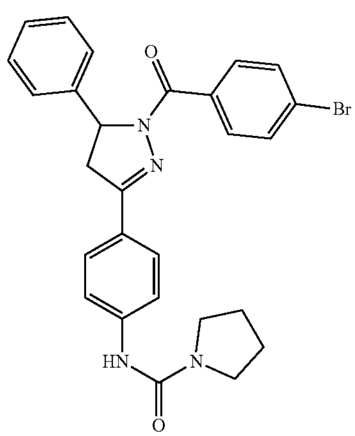 [SMILES: O=C(Nc1ccc(C2=NN(C(=O)c3ccc(Br)cc3)C(c3ccccc3)C2)cc1)N1CCCC1] | >10 | 4.94 | 4.6 | 5.28 | 65.01 |

TABLE 2
SAR: activity is retained across R1 scope
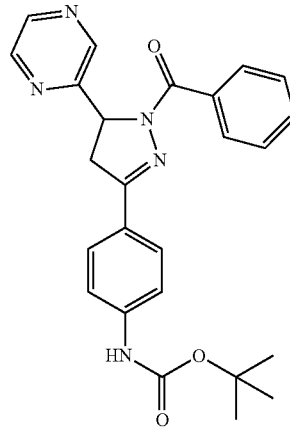
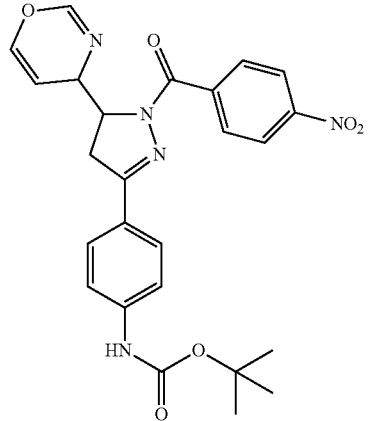
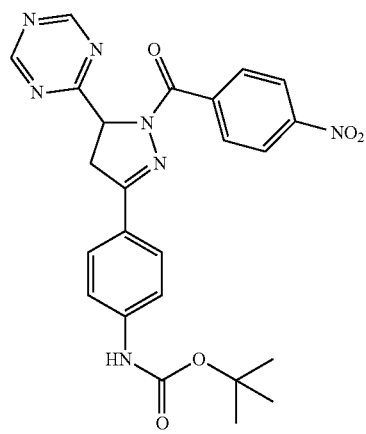 [SMILES: CC(C)(C)OC(=O)Nc1ccc(C2=NN(C(=O)c3ccc([N+](=O)[O-])cc3)C(c3ncncn3)C2)cc1]
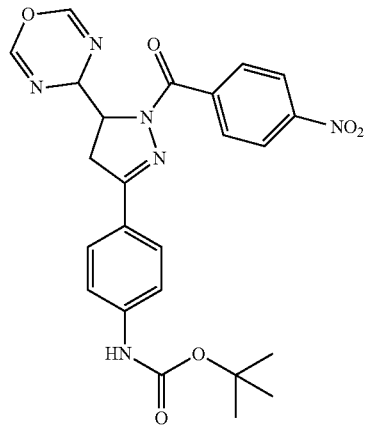
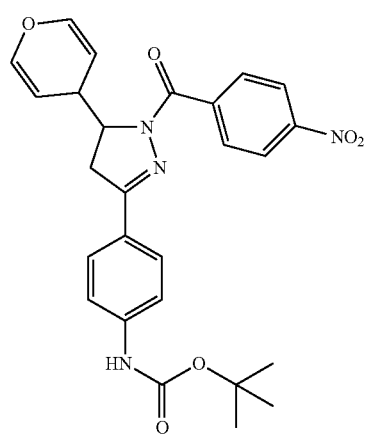 [SMILES: CC(C)(C)OC(=O)Nc1ccc(C2=NN(C(=O)c3ccc([N+](=O)[O-])cc3)C(C3C=COC=C3)C2)cc1]
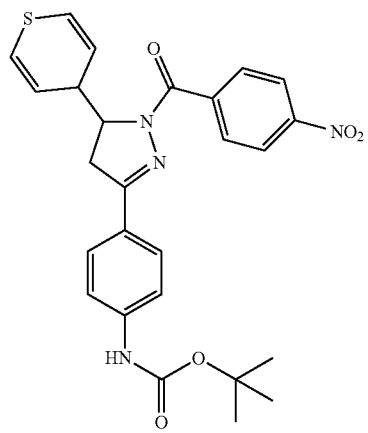 [SMILES: CC(C)(C)OC(=O)Nc1ccc(C2=NN(C(=O)c3ccc([N+](=O)[O-])cc3)C(C3C=CSC=C3)C2)cc1]

TABLE 2-continued
SAR: activity is retained across R1 scope
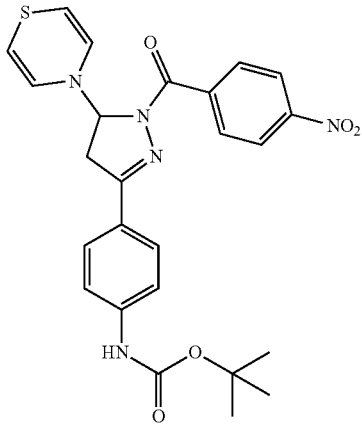 [SMILES: CC(C)(C)OC(=O)Nc1ccc(C2=NN(C(=O)c3ccc([N+](=O)[O-])cc3)C(N3C=CSC=C3)C2)cc1]
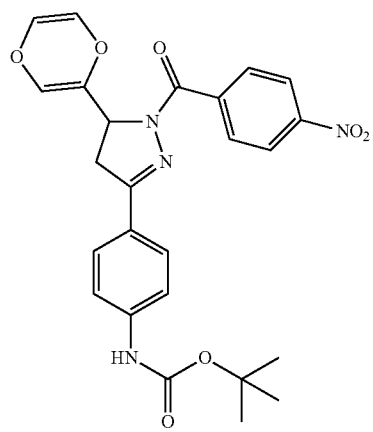 [SMILES: CC(C)(C)OC(=O)Nc1ccc(C2=NN(C(=O)c3ccc([N+](=O)[O-])cc3)C(C3=COC=CO3)C2)cc1]
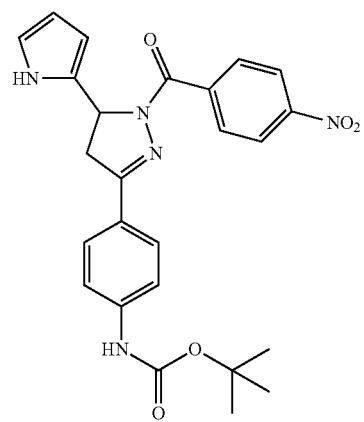
TABLE 2-continued
SAR: activity is retained across R1 scope
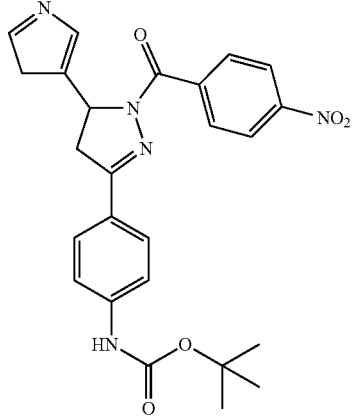
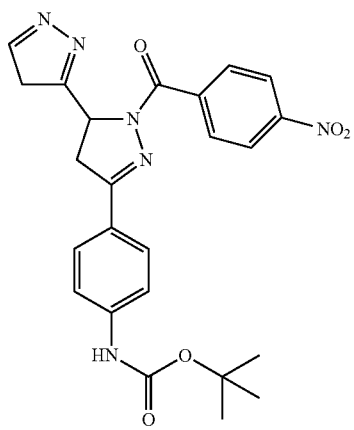 [SMILES: CC(C)(C)OC(=O)Nc1ccc(C2=NN(C(=O)c3ccc([N+](=O)[O-])cc3)C(C3=NN=CC3)C2)cc1]
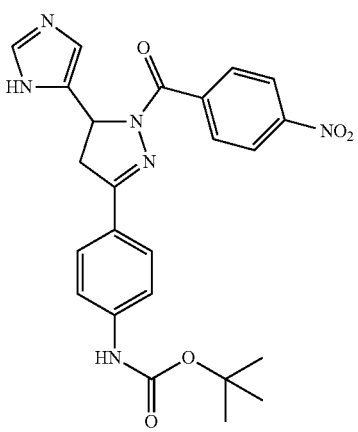 [SMILES: CC(C)(C)OC(=O)Nc1ccc(C2=NN(C(=O)c3ccc([N+](=O)[O-])cc3)C(c3cnc[nH]3)C2)cc1]

TABLE 2-continued
SAR: activity is retained across R1 scope
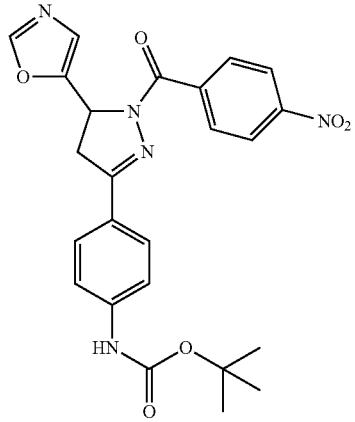 [SMILES: CC(C)(C)OC(=O)Nc1ccc(C2=NN(C(=O)c3ccc([N+](=O)[O-])cc3)C(c3cnco3)C2)cc1]
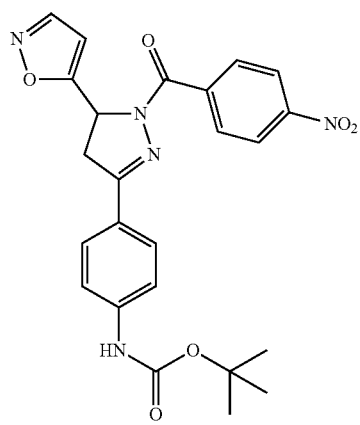 [SMILES: CC(C)(C)OC(=O)Nc1ccc(C2=NN(C(=O)c3ccc([N+](=O)[O-])cc3)C(c3ccno3)C2)cc1]
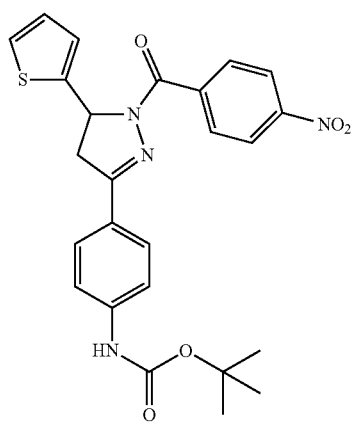 [SMILES: CC(C)(C)OC(=O)Nc1ccc(C2=NN(C(=O)c3ccc([N+](=O)[O-])cc3)C(c3cccs3)C2)cc1]
TABLE 2-continued
SAR: activity is retained across R1 scope
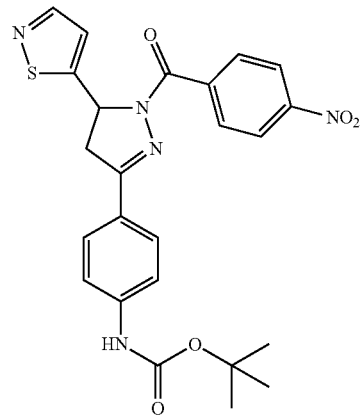
TABLE 3
SAR: activity is retained across R3 scope
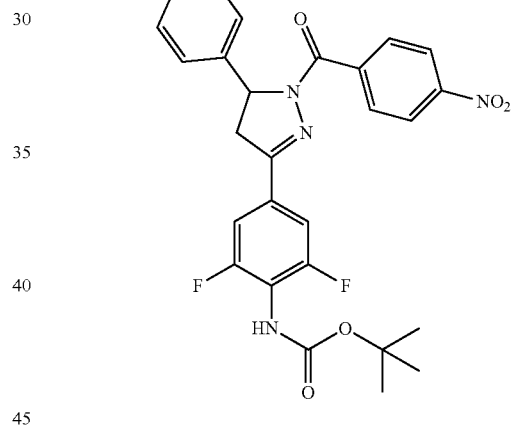
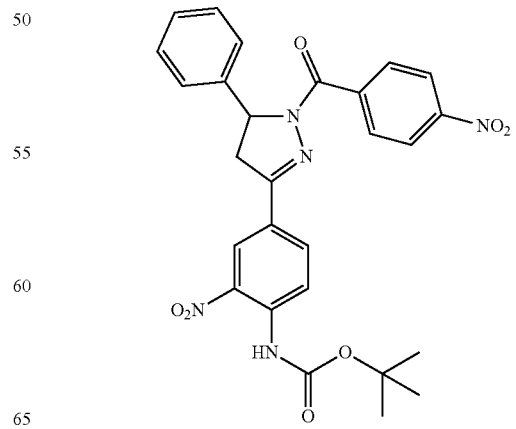

TABLE 3-continued
SAR: activity is retained across R3 scope
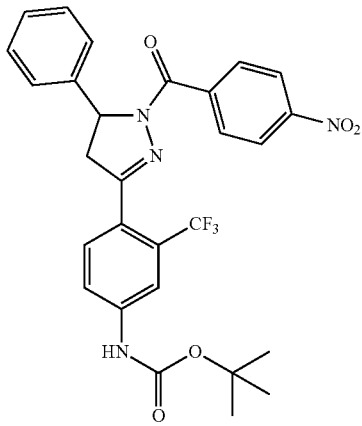 [SMILES: CC(C)(C)OC(=O)Nc1ccc(C2=NN(C(=O)c3ccc([N+](=O)[O-])cc3)C(c3ccccc3)C2)c(C(F)(F)F)c1]
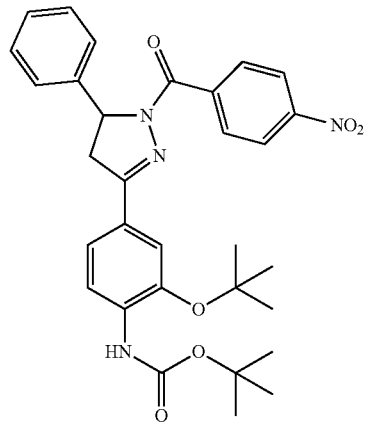
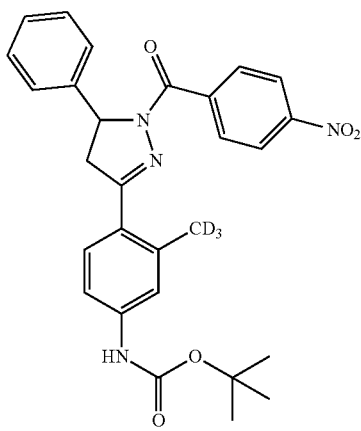 [SMILES: [2H]C([2H])([2H])c1cc(NC(=O)OC(C)(C)C)ccc1C1=NN(C(=O)c2ccc([N+](=O)[O-])cc2)C(c2ccccc2)C1]
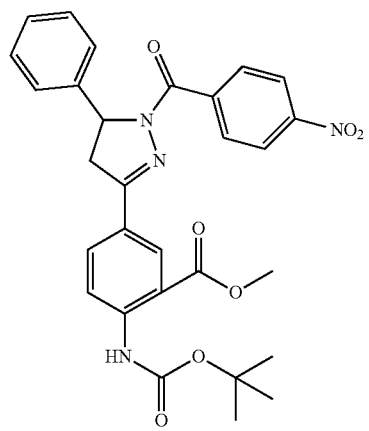
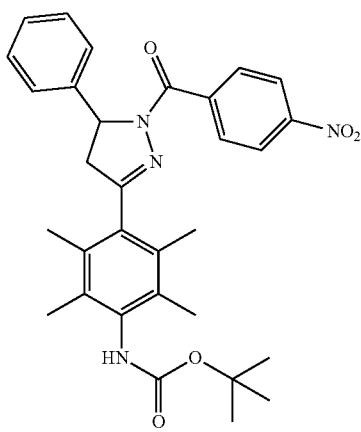 [SMILES: Cc1c(C)c(C2=NN(C(=O)c3ccc([N+](=O)[O-])cc3)C(c3ccccc3)C2)c(C)c(C)c1NC(=O)OC(C)(C)C]
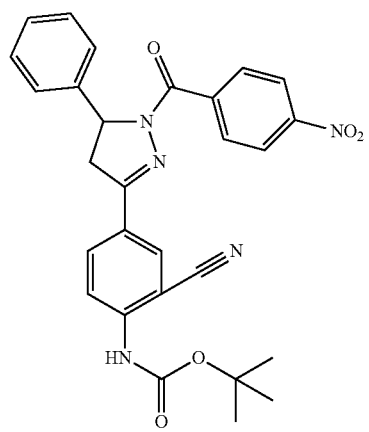 [SMILES: CC(C)(C)OC(=O)Nc1ccc(C2=NN(C(=O)c3ccc([N+](=O)[O-])cc3)C(c3ccccc3)C2)cc1C#N]

TABLE 4
SAR: activity is retained across R4 scope
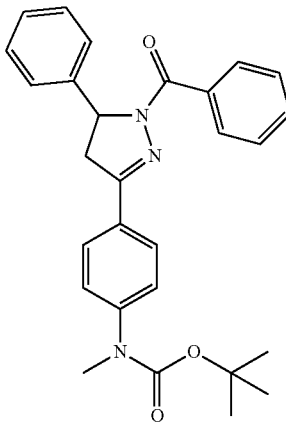
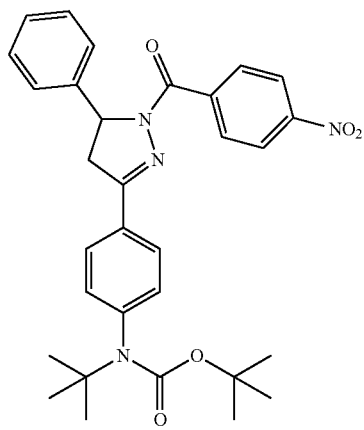 [SMILES: CC(C)(C)OC(=O)N(c1ccc(C2=NN(C(=O)c3ccc([N+](=O)[O-])cc3)C(c3ccccc3)C2)cc1)C(C)(C)C]
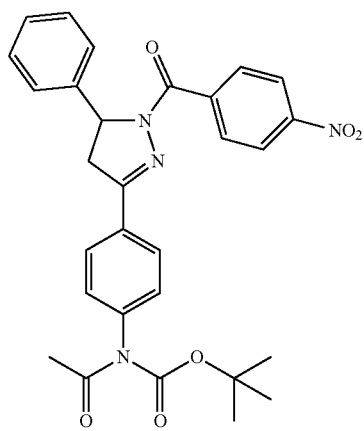 [SMILES: CC(=O)N(C(=O)OC(C)(C)C)c1ccc(C2=NN(C(=O)c3ccc([N+](=O)[O-])cc3)C(c3ccccc3)C2)cc1]
TABLE 4-continued
SAR: activity is retained across R4 scope
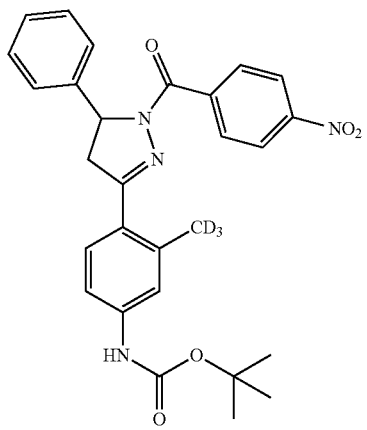 [SMILES: [2H]C([2H])([2H])c1cc(NC(=O)OC(C)(C)C)ccc1C1=NN(C(=O)c2ccc([N+](=O)[O-])cc2)C(c2ccccc2)C1]
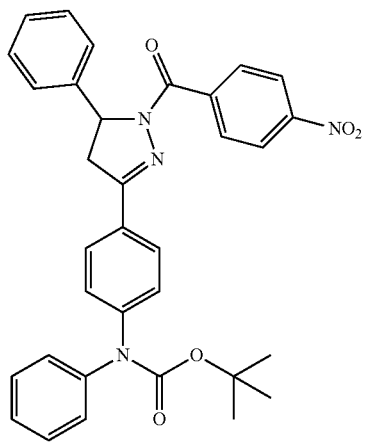 [SMILES: CC(C)(C)OC(=O)N(c1ccccc1)c1ccc(C2=NN(C(=O)c3ccc([N+](=O)[O-])cc3)C(c3ccccc3)C2)cc1]
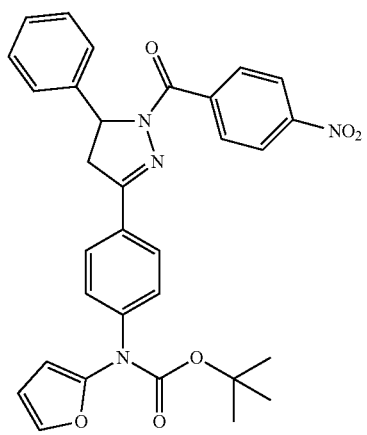 [SMILES: CC(C)(C)OC(=O)N(c1ccc(C2=NN(C(=O)c3ccc([N+](=O)[O-])cc3)C(c3ccccc3)C2)cc1)c1ccco1]

What is claimed is:

1. A method of selectively inducing autophagy, comprising treating a person in need thereof with a pharmaceutical composition comprising a compound of structure I:

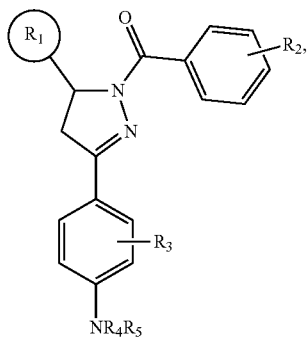

wherein

R1 is 2- or 3-furanyl or phenyl, or 2-, 3- or 4-pyridine;

R2 is a 1 para substituent selected from halogen, NO$_2$, N, C1-C4 alkyl, C1-C4 alkoxy, C1-C4 carbonyl, C1-C4 carboxyl, C1-C4 cyano, C1-C4 sulfinyl, and C1-C4 sulfonyl, each optionally fluorinated;

R3 is 0 substituents;

R4 is H; and

R5 is SO$_2$R or CO$_2$R, wherein R is C1-C4 alkyl, optionally fluorinated;

or a salt, hydrate, or stereoisomer thereof.

2. The method of claim 1, wherein R1 is 2- or 3-furanyl.

3. The method of claim 1, wherein R1 is phenyl.

4. The method of claim 1, wherein R1 is 2-, 3- or 4-pyridine.

5. The method of claim 1, wherein R2 is a 1 para substituent that is halogen.

6. The method of claim 1, wherein R2 is a 1 para substituent that is NO$_2$.

7. The method of claim 1, wherein R2 is a 1 para substituent that is N.

8. The method of claim 1, wherein R2 is a 1 para substituent that is C1-C4 alkyl, optionally fluorinated.

9. The method of claim 1, wherein R2 is a 1 para substituent that is C1-C4 alkoxy, optionally fluorinated.

10. The method of claim 1, wherein R2 is a 1 para substituent that is —C4 carbonyl, optionally fluorinated.

11. The method of claim 1, wherein R2 is a 1 para substituent that is C1-C4 carboxyl, optionally fluorinated.

12. The method of claim 1, wherein R2 is a 1 para substituent that is C1-C4 cyano, optionally fluorinated.

13. The method of claim 1, wherein R2 is a 1 para substituent that is C1-C4 sulfinyl, optionally fluorinated.

14. The method of claim 1, wherein R2 is a 1 para substituent that is C1-C4 sulfonyl, optionally fluorinated.

15. The method of claim 1, wherein R5 is SO$_2$R, wherein R is C1-C4 alkyl, optionally fluorinated.

16. The method of claim 1, wherein R5 is CO$_2$R, wherein R is C1-C4 alkyl, optionally fluorinated.

17. The method of claim 1, wherein the compound is selected from:

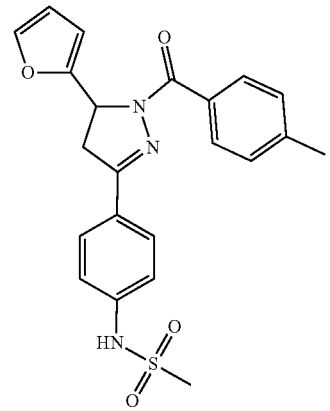

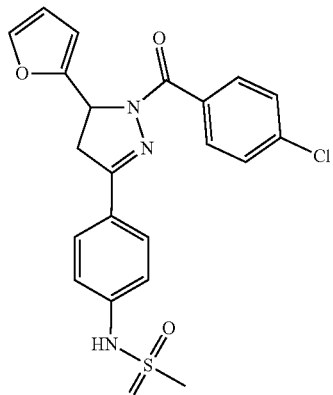

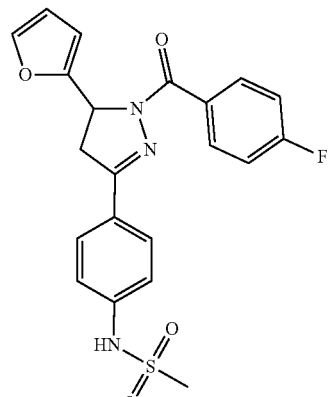

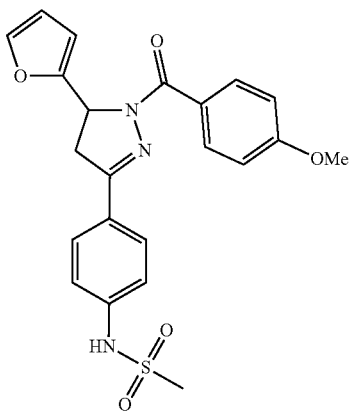

91
-continued
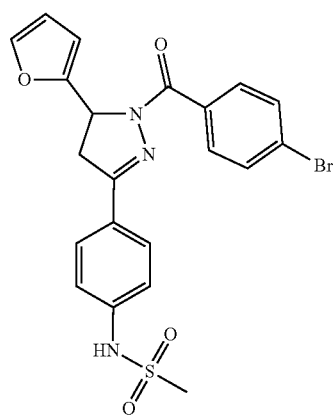
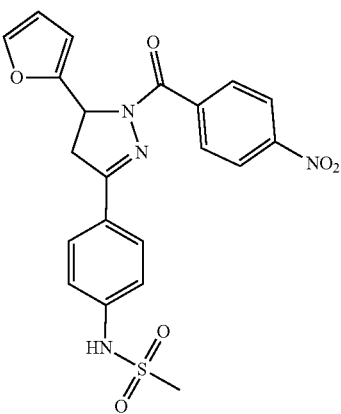
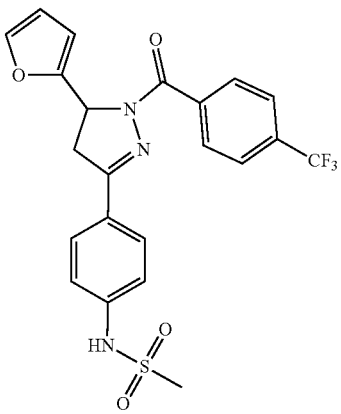
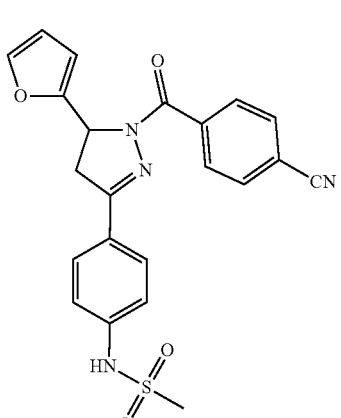
92
-continued
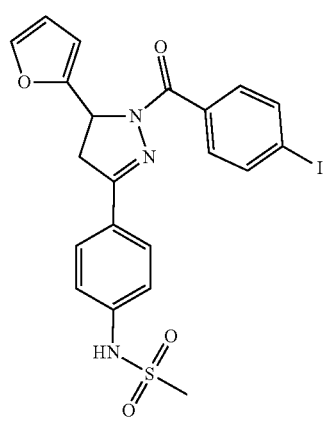
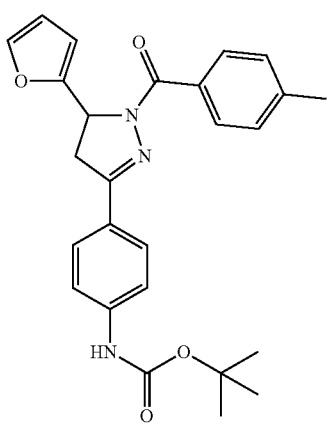
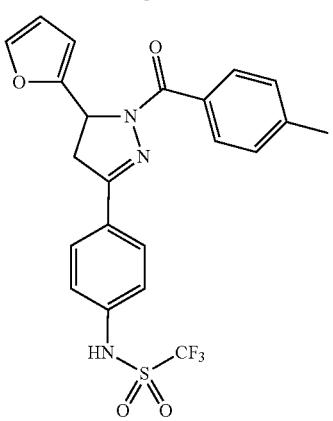
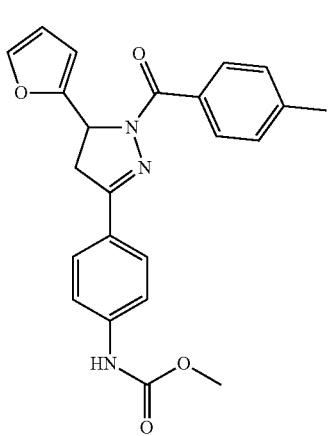

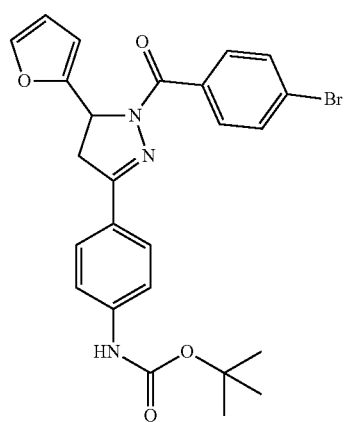
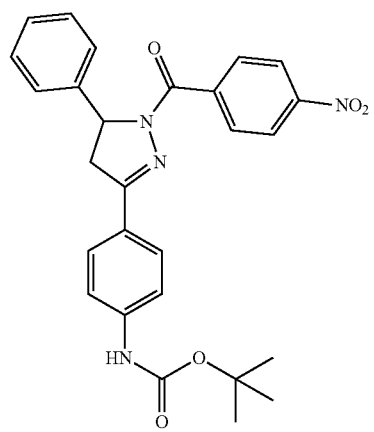
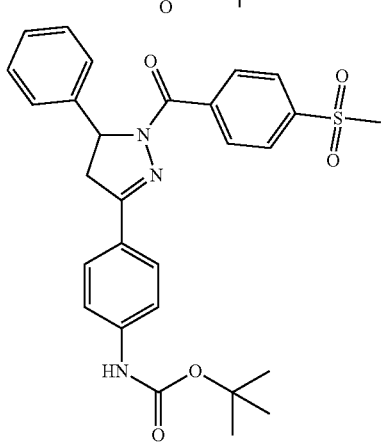
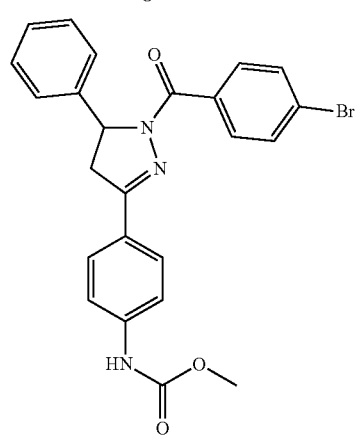
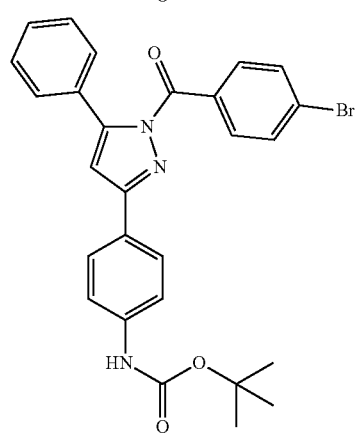

95
-continued
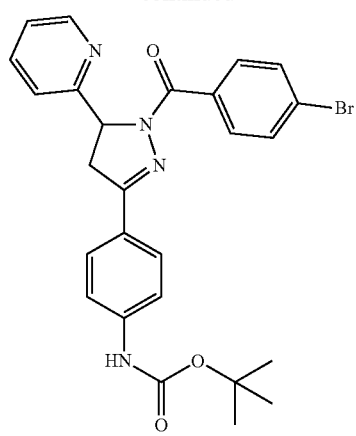
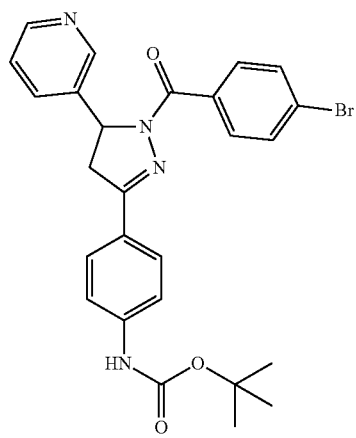
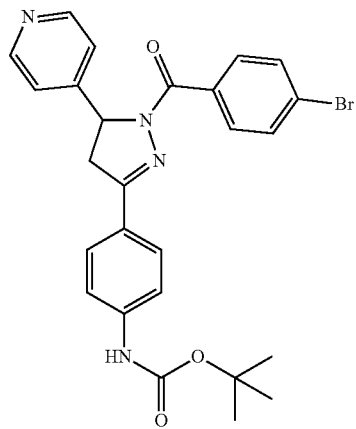
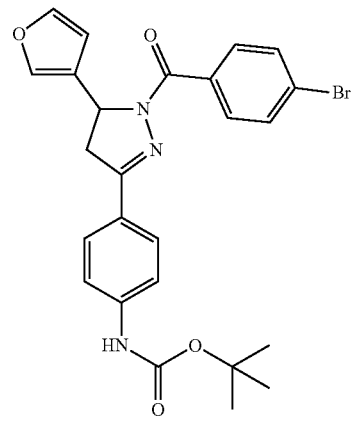
96
-continued
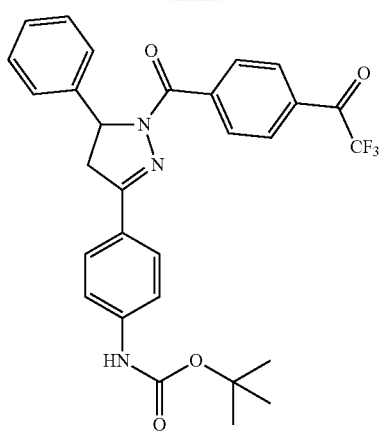
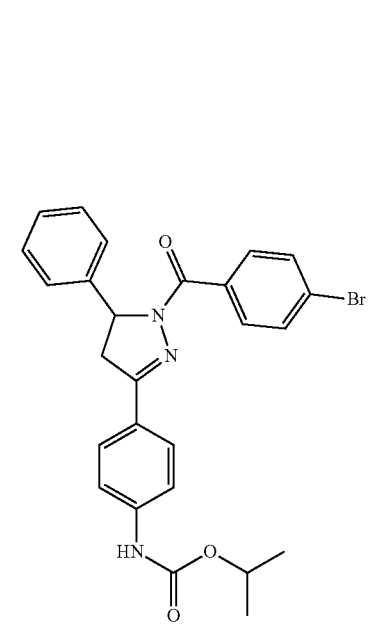
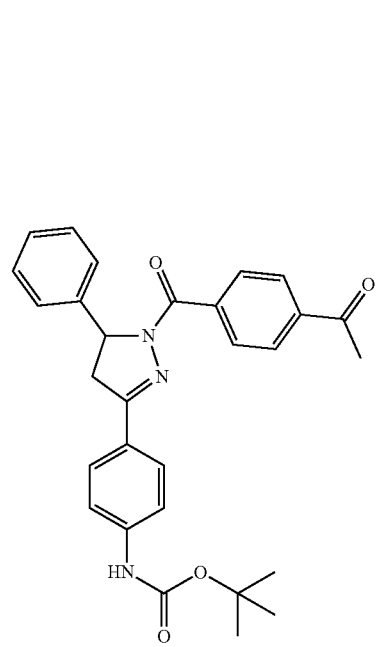

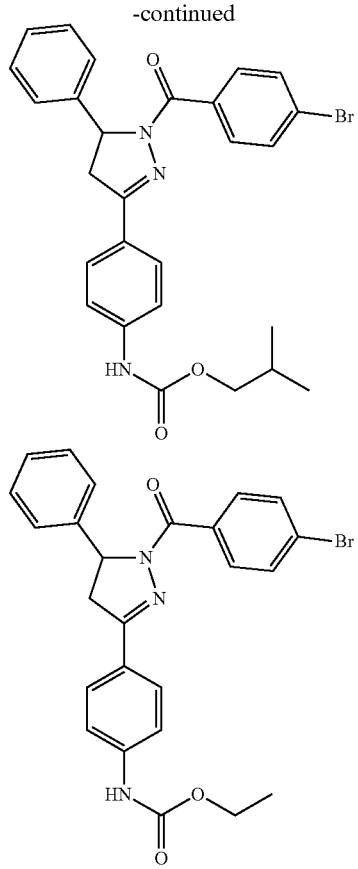
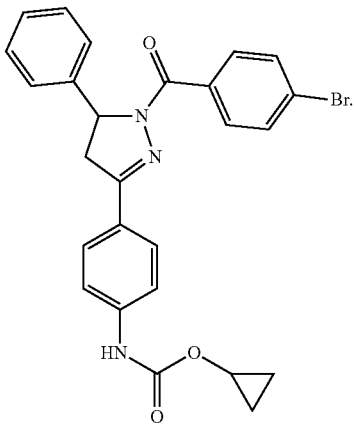
18. The method of claim 1 wherein the person is in need of treatment for diabetes, infection, cancer, neurodegenerative disease or aging.
19. The method of claim 1 wherein the person is in need of treatment for cancer.
20. The method of claim 1 wherein the person is in need of treatment for Zika virus infection.
* * * * *